United States Patent
Johnson et al.

(10) Patent No.: US 11,543,885 B2
(45) Date of Patent: Jan. 3, 2023

(54) GRAPHICAL EMOTION SYMBOL DETERMINATION BASED ON BRAIN MEASUREMENT DATA FOR USE DURING AN ELECTRONIC MESSAGING SESSION

(71) Applicant: HI LLC, Los Angeles, CA (US)

(72) Inventors: Bryan Johnson, Culver City, CA (US); Ryan Field, Culver City, CA (US)

(73) Assignee: HI LLC, Los Angeles, CA (US)

( * ) Notice: Subject to any disclaimer, the term of this patent is extended or adjusted under 35 U.S.C. 154(b) by 0 days.

(21) Appl. No.: 17/726,747

(22) Filed: Apr. 22, 2022

(65) Prior Publication Data

US 2022/0382372 A1   Dec. 1, 2022

Related U.S. Application Data

(60) Provisional application No. 63/297,976, filed on Jan. 10, 2022, provisional application No. 63/193,473, filed on May 26, 2021.

(51) Int. Cl.
*G06F 3/01* (2006.01)
*H04L 51/08* (2022.01)
*G06T 11/00* (2006.01)
*G06F 3/03* (2006.01)

(52) U.S. Cl.
CPC ............ *G06F 3/015* (2013.01); *G06F 3/0304* (2013.01); *G06T 11/00* (2013.01); *H04L 51/08* (2013.01)

(58) Field of Classification Search
None
See application file for complete search history.

(56) References Cited

U.S. PATENT DOCUMENTS

| | | |
|---|---|---|
| 5,853,370 A | 12/1998 | Chance et al. |
| 6,240,309 B1 | 5/2001 | Yamashita et al. |
| 6,384,663 B2 | 5/2002 | Cova et al. |
| 6,640,133 B2 | 10/2003 | Yamashita |
| 6,683,294 B1 | 1/2004 | Herbert et al. |
| 7,356,365 B2 | 4/2008 | Schurman |
| 7,547,872 B2 | 6/2009 | Niclass et al. |
| 7,774,047 B2 | 8/2010 | Yamashita et al. |

(Continued)

FOREIGN PATENT DOCUMENTS

WO   2018033751   2/2018

OTHER PUBLICATIONS

"emojipedia.org", https://emojipedia.org (accessed May 27, 2021).

(Continued)

*Primary Examiner* — Ifedayo B Iluyomade
(74) *Attorney, Agent, or Firm* — ALG Intellectual Property, LLC

(57) ABSTRACT

An illustrative system includes a brain interface system configured to be worn by a user and to output brain measurement data representative of brain activity of the user while the user is engaged in an electronic messaging session provided by an electronic messaging platform and a computing device configured to obtain the brain measurement data, determine, based on the brain measurement data, a graphical emotion symbol representative of a mental state of the user while the user is engaged in the electronic messaging session, and provide the graphical emotion symbol for use during the electronic messaging session.

19 Claims, 16 Drawing Sheets

(56) References Cited

U.S. PATENT DOCUMENTS

| | | |
|---|---|---|
| 8,026,471 B2 | 9/2011 | Itzler |
| 8,078,250 B2 | 12/2011 | Chen et al. |
| 8,082,015 B2 | 12/2011 | Vodh et al. |
| 8,633,431 B2 | 1/2014 | Kim |
| 8,817,257 B2 | 8/2014 | Herve |
| 9,058,081 B2 | 6/2015 | Baxter |
| 9,076,707 B2 | 7/2015 | Harmon |
| 9,131,861 B2 | 9/2015 | Ince et al. |
| 9,316,735 B2 | 4/2016 | Baxter |
| 9,401,448 B2 | 7/2016 | Bienfang et al. |
| 9,419,635 B2 | 8/2016 | Kumar et al. |
| 9,442,201 B2 | 9/2016 | Schmand et al. |
| 9,529,079 B1 | 12/2016 | Droz |
| 9,574,936 B2 | 2/2017 | Heinonen |
| 9,946,344 B2 | 4/2018 | Ayaz et al. |
| D817,553 S | 5/2018 | Aaskov et al. |
| D825,112 S | 8/2018 | Saez |
| 10,158,038 B1 | 12/2018 | Do Valle et al. |
| 10,340,408 B1 | 7/2019 | Katnani |
| 10,424,683 B1 | 9/2019 | Do Valle |
| 10,515,993 B2 | 12/2019 | Field et al. |
| 10,579,742 B1 | 3/2020 | Fernandez |
| 10,627,460 B2 | 4/2020 | Alford et al. |
| 10,697,829 B2 | 6/2020 | Delic |
| 10,772,561 B2 | 9/2020 | Donaldson |
| 10,809,796 B2 | 10/2020 | Armstrong-Muntner |
| 10,912,504 B2 | 2/2021 | Nakaji |
| 10,976,386 B2 | 4/2021 | Alford |
| 10,983,177 B2 | 4/2021 | Jiménez-Martínez |
| 10,996,293 B2 | 5/2021 | Mohseni |
| 11,006,876 B2 | 5/2021 | Johnson |
| 11,006,878 B2 | 5/2021 | Johnson |
| 2007/0083097 A1 | 4/2007 | Fujiwara |
| 2009/0012402 A1 | 1/2009 | Mintz |
| 2010/0219820 A1 | 9/2010 | Skidmore et al. |
| 2011/0208575 A1 | 8/2011 | Shoureshi et al. |
| 2013/0342835 A1 | 12/2013 | Blacksberg |
| 2014/0191115 A1 | 7/2014 | Webster et al. |
| 2014/0217264 A1 | 8/2014 | Shepard |
| 2014/0275891 A1 | 9/2014 | Muehlemann et al. |
| 2015/0038811 A1 | 2/2015 | Asaka |
| 2015/0041625 A1 | 2/2015 | Dutton |
| 2015/0054111 A1 | 2/2015 | Niclass et al. |
| 2015/0077279 A1 | 3/2015 | Song |
| 2015/0150505 A1 | 6/2015 | Kaskoun et al. |
| 2015/0327777 A1 | 11/2015 | Kostic et al. |
| 2015/0364635 A1 | 12/2015 | Bodlovic et al. |
| 2017/0030769 A1 | 2/2017 | Clemens et al. |
| 2017/0042439 A1 | 2/2017 | Yeow et al. |
| 2017/0052065 A1 | 2/2017 | Sharma et al. |
| 2017/0176596 A1 | 6/2017 | Shpunt et al. |
| 2017/0179173 A1 | 6/2017 | Mandai et al. |
| 2017/0202518 A1 | 7/2017 | Furman et al. |
| 2017/0281086 A1 | 10/2017 | Donaldson |
| 2017/0363467 A1 | 12/2017 | Clemens et al. |
| 2017/0367650 A1 | 12/2017 | Wallois |
| 2018/0014741 A1 | 1/2018 | Chou |
| 2018/0027196 A1 | 1/2018 | Yang et al. |
| 2018/0035938 A1 | 2/2018 | El Kaliouby et al. |
| 2018/0039053 A1 | 2/2018 | Kremer et al. |
| 2018/0070830 A1 | 3/2018 | Sutin et al. |
| 2018/0070831 A1 | 3/2018 | Sutin et al. |
| 2018/0089848 A1 | 3/2018 | Yang et al. |
| 2019/0091483 A1 | 3/2019 | Deckert |
| 2019/0113385 A1 | 4/2019 | Fukuchi |
| 2019/0175068 A1 | 6/2019 | Everdell |
| 2019/0355861 A1 | 11/2019 | Katnani |
| 2019/0363210 A1 | 11/2019 | Do Valle |
| 2019/0384392 A1 | 12/2019 | Aimone et al. |
| 2019/0388018 A1 | 12/2019 | Horstmeyer |
| 2019/0391213 A1 | 12/2019 | Alford |
| 2020/0056263 A1 | 2/2020 | Bhattacharyya |
| 2020/0057116 A1 | 2/2020 | Zorzos et al. |
| 2020/0060542 A1 | 2/2020 | Alford |
| 2020/0088811 A1 | 3/2020 | Mohseni |
| 2020/0109481 A1 | 4/2020 | Sobek |
| 2020/0116838 A1 | 4/2020 | Erdogan |
| 2020/0123416 A1 | 4/2020 | Bhattacharyya |
| 2020/0191883 A1 | 6/2020 | Bhattacharyya |
| 2020/0196932 A1 | 6/2020 | Johnson |
| 2020/0241094 A1 | 7/2020 | Alford |
| 2020/0253479 A1 | 8/2020 | Nurmikko |
| 2020/0256929 A1 | 8/2020 | Ledbetter et al. |
| 2020/0309873 A1 | 10/2020 | Ledbetter et al. |
| 2020/0315510 A1 | 10/2020 | Johnson |
| 2020/0334559 A1 | 10/2020 | Anderson |
| 2020/0337624 A1 | 10/2020 | Johnson |
| 2020/0341081 A1 | 10/2020 | Mohseni et al. |
| 2020/0348368 A1 | 11/2020 | Garber et al. |
| 2020/0381128 A1 | 12/2020 | Pratt |
| 2020/0390358 A1* | 12/2020 | Johnson ............... A61B 5/0059 |
| 2020/0400763 A1 | 12/2020 | Pratt |
| 2021/0015385 A1 | 1/2021 | Katnani |
| 2021/0011094 A1 | 2/2021 | Bednarke |
| 2021/0041512 A1 | 2/2021 | Pratt |
| 2021/0063510 A1 | 3/2021 | Ledbetter |
| 2021/0076090 A1 | 3/2021 | Aimone et al. |
| 2021/0223864 A1* | 7/2021 | Forsland ................ G06F 1/163 |

OTHER PUBLICATIONS

"scienceofpeople.com/emojis", https://www.scienceofpeople.com/emojis/ (accessed May 27, 2021).

Alayed, et al., "Characterization of a Time-Resolved Diffuse Optical Spectroscopy Prototype Using Low-Cost, Compact Single Photon Avalanche Detectors for Tissue Optics Applications", Sensors 2018, 18, 3680; doi:10.3390/s18113680, Oct. 29, 2018.

Alem, O. et al., "Magnetic Field Imaging with Microfabricated Optically-Pumped Magnetometers", Opt. Express 25, 7849-7858 (2017).

Ban, et al., "Kernel Flow: a high channel count scalable TD-fNIRS system", https://www.spiedigitallibrary.org/conference-proceedings-of-spie Proc. of SPIE vol. 11663, 116630B doi: 10.1117/12.2582888, Mar. 5, 2021.

Ban, et al., "Kernel Flow: a high channel count scalable time-domain functional near-infrared spectroscopy system", https://www.spiedigitallibraryorg/journals/Journal-of-Biomedical-Optics on Jan. 18, 2022.

Baranga, et al., "An Atomic Magnetometer for Brain Activity Imaging", Real Time Conference 2005. 14th IEEE-NPSS. pp. 417-418, 2005.

Borna, A. et al., "A 20-Channel Magnetoencephalography System Based on Optically Pumped Magnetometers", Physics in Medicine & Biology 62.23 (2017): 8909.

Borna, et al., "Non-lnvasive Functional-Brain-lmaging with an OPM-based Magnetoencephalography System", PLoS One 15 (1): e0227684. https://doi.org/10.1371/journal.pone.0227684, 2014.

Boto, E. et al., "Moving Magnetoencephalography Towards Real World Applications with a Wearable System", Nature, vol. 555, pp. 657-661, 2018.

Budker, D. et al., "Optical Magnetometry", Nature Physics, 2008, https://arxiv.org/abs/physics/0611246v1.

Contini, et al., "Photon migration through a turbid slab described by a model based on diffusion approximation. I. Theory", Appl. Opt. 36(19), 4587 (1997).

Di Sieno, et al., "Probe-hosted large area silicon photomultiplier and high-throughput timing electronics for enhanced performance time-domain functional near-infrared spectroscopy", Biomed. Opt. Express 11(11), 6389 (2020).

Fishburn, et al., "Temporal Derivative Distribution Repair (TDDR): A motion correction method for fNIRS", Neuroimage. Jan. 1, 2019; 184: 171-179. doi:10.1016/j.neuroimage.2018.09.025.

Hamalainen, M. et al., "Magnetoencephalograph—Theory, Instrumentation, and Applications to Noninvasive Studies of the Working Human Brain", Reviews of Modern Physics, vol. 65, Issue 2. 413-497 (1993).

Hill, R.M. et al., "A Tool for Functional Brain Imaging with Lifespan Compliance", Nature Communications (2019) 10:4785. https://doi.org/10.1038/s41467-019-12486-x.

(56) References Cited

OTHER PUBLICATIONS

Hill, R.M. et al., "Multi-Channel Whole-Head OPM-MEG: Helmet Design and a Comparison with a Conventional System", NeuroImage vol. 219 (2020) 116995. https://doi.org/10.1016/j.neuroimage.2020.116995.

Huppert, et al., "HomER: a review of time-series analysis methods for near-infrared spectroscopy of the brain", Appl. Opt. 48(10), D280 (2009).

Iivanainen, et al., "Measuring MEG closer to the brain: Performance of on-scalp sensor arrays", NeuroImage 147 (2017) 542-553 http://dx.doi.org/10.1016/j.neuroimage.2016.12.048.

Iivanainen, et al., "On-scalp MEG system utilizing an actively shielded array of optically-pumped magnetometers", NeuroImage 194 (2019) 244-258 https://doi.org/10.1016/j.neuroimage.2019.03.022.

Kienle, et al., "Improved solutions of the steady-state and the time-resolved diffusion equations for reflectance from a semi-infinite turbid medium", J. Opt. Soc. Am. A 14(1), 246 (1997).

Kim, K. et al., "Multi-Channel Atomic Magnetometer for Magnetoencephalography: A Configuration Study", NeuroImage 89 (2014) 143-151 https://physics.princeton.edu/romalis/papers/Kim_2014.pdf.

Konugolu, et al., "Broadband (600-1350 nm) Time-Resolved Diffuse Optical Spectrometer for Clinical Use", IEEE Journal of Selected Topics in Quantum Electronics, vol. 22, No. 3, May/Jun. 2016.

Lacerenza, et al., "Wearable and wireless time-domain near-infrared spectroscopy system for brain and muscle hemodynamic monitoring", Biomed. Opt. Express 11(10), 5934 (2020).

Lange, et al., "Clinical Brain Monitoring with Time Domain NIRS: A Review and Future Perspectives", Applied Sciences 9(8), 1612 (2019).

Lange, et al., "MAESTROS: A Multiwavelength Time-Domain NIRS System to Monitor Changes in Oxygenation and Oxidation State of Cytochrome-C-Oxidase", IEEE J. Select Topics Quantum Electron. 25(1), 1-12 (2019).

Martelli, et al., "Optimal estimation reconstruction of the optical properties of a two-layered tissue phantom from time-resolved single-distance measurements", Journal of Biomedical Optics 20(11), 115001 (Nov. 2015).

Mellinger, et al., "An MEG-based Brain-Computer Interface (BCI)", Neuroimage. Jul. 1, 2007; 36(3): 581-593.

Mora, et al., "Fast silicon photomultiplier improves signal harvesting and reduces complexity in time-domain diffuse optics", Opt. Express 23(11), 13937 (2015).

Pifferi, et al., "Performance assessment of photon migration instruments: the MEDPHOT protocol", Applied Optics, 44(11), 2104-2114, 2005.

Pineda, et al., "Learning to Control Brain Rhythms: Making A Brain-Computer Interface Possible", IEEE Transactions on Neural Systems and Rehabilitation Engineering Jun. 2003;11(2):181-4 (2003).

Pour, et al., "Brain-Computer Interface: Next Generation Thought Controlled Distributed Video Game Development Platform", 2008 IEEE Symposium on Computational Intelligence and Games (CIG'08) pp. 251-257 (2008).

Prahl, et al., "Optical Absorption of Hemoglobin", http://omlc.ogi.edu/spectra/hemoglobin/index.html, 1999.

Pratt, et al., "Kernel Flux: A Whole-Head 432-Magnetometer Optically-Pumped Magnetoencephalography (OP-MEG) System For Brain Activity Imaging During Natural Human Experiences", SPIE Photonics West Conference (Mar. 6, 2021).

Re, et al., "Multi-channel medical device for time domain functional near infrared spectroscopy based on wavelength space multiplexing", Biomed. Opt. Express 4(10), 2231 (2013).

Renna, et al., "Eight-Wavelength, Dual Detection Channel Instrument for Near-Infrared Time-Resolved Diffuse Optica Spectroscopy", IEEE J. Select. Topics Quantum Electron. 25(1), 1-11 (2019).

Robinson, et al., "Developing Next-Generation Brain Sensing Technologies—A Review", IEEE Sensors Journal, vol. 19, No. 22, Nov. 15, 2019.

Sander, T.H. et al., "Magnetoencephalography with a Chip-Scale Atomic Magnetometer", Biomed Opt Express. 2012; 3(5):981-90.

Tierney, T.M. et al., "Cognitive Neuroscience Using Wearable Magnetometer Arrays: Non-Invasive Assessment of Language Function", NeuroImage vol. 181 (2018) pp. 513-520. https://doi.org/10.1016/j.neuroimage.2018.07.035.

Torricelli, et al., "Time domain functional NIRS imaging for human brain mapping", NeuroImage 85, 28-50 (2014).

Wabnitz, et al., "Depth-selective data analysis for time-domain fNIRS: moments vs. time windows", Biomed. Opt. Express 11(8), 4224 (2020).

Wabnitz, et al., "Performance assessment of time-domain optical brain imagers, part 1: basic instrumental performance protocol", Journal of Biomedical Optics 19(8), 086010 (Aug. 2014).

Wabnitz, et al., "Performance assessment of time-domain optical brain imagers, part 2: nEUROPt protocol", Journal of Biomedical Optics 19(8), 086012 (Aug. 2014).

Wojtkiewicz, et al., "Self-calibrating time-resolved near infrared spectroscopy", Biomed. Opt. Express 10(5), 2657 (2019).

Wolpaw, et al., "An EEG-based brain-computer interface for cursor control", Electroencephalography and clinical Neurophysiology, 1991, 78:252-259.

Zetter, R. et al., "Optical Co-registration of MRI and On-scalp MEG", Scientific Reports (2019) 9:5490. https://doi.org/10.1038/S41598-019-41763-4.

Zucchelli, et al., "Method for the discrimination of superficial and deep absorption variations by time domain fNIRS", 2013 OSA Dec. 1, 2013 | vol. 4, No. 12 | DOI:10.1364/BOE.4.002893 | Biomedical Optics Express 2893, 2013.

"International Search Report and Written Opinion received in International Application No. PCT/US2022/026020 dated Sep. 26, 2022".

"Partial International Search Report received in International Application No. PCT/US2022/026020, dated Aug. 5, 2022".

Xu, et al., "A 655 µW Silicon Photomultiplier-Based NIRS/EEG/EIT Monitoring ASIC for Wearable Functional Brain Imaging", IEEE Transactions on Biomedical Circuitsand Systems, IEEE, US, vol. 12, No. 6, Dec. 1, 2018.

* cited by examiner

GRAPHICAL EMOTION SYMBOL DETERMINATION BASED ON BRAIN MEASUREMENT DATA FOR USE DURING AN ELECTRONIC MESSAGING SESSION

RELATED APPLICATIONS

The present application claims priority under 35 U.S.C. § 119(e) to U.S. Provisional Patent Application No. 63/297,976, filed on Jan. 10, 2022, and to U.S. Provisional Patent Application No. 63/193,473, filed on May 26, 2021, each of which is incorporated herein by reference in its entirety.

BACKGROUND INFORMATION

Electronic messaging platforms, such as remote online video conferencing platforms, online chat services, and other cloud-based peer-to-peer software platforms, provide users with the ability to instantly communicate and/or otherwise share information.

Some electronic messaging platforms offer the ability for users to include emojis in their messages. These emojis may allow a user to graphically express a reaction, an emotion, an idea, etc.

Unfortunately, during the flow of an electronic conversation, it may be difficult for a user to select or create an emoji that adequately conveys his or her feelings, especially when the user can choose from a large library of emojis and/or is pressed for time. Accordingly, many users default to using a select few emojis during their electronic conversations, and the selected emoji is typically a random choice.

Moreover, manual selection and/or creation of an emoji is by nature subjective, and often does not accurately convey how the user is really feeling. For example, when selecting or creating an emoji, a user may often fail to consider other factors, such as feeling tired, hungry, stressed, anxious, and/or afraid. To illustrate, when a user is tired or stressed out, the user may be particularity vulnerable, thereby making it difficult to assess his or her emotional feelings during an online chatting service and to represent such feelings using an appropriate emoji.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Graphical emotion symbol determination based on brain measurement data for use during an electronic messaging session is described herein. For example, an illustrative system may include a brain interface system and a computing device. The brain interface system may be configured to be worn by a user and to output brain measurement data representative of brain activity of the user while the user is engaged in an electronic messaging session provided by an electronic messaging platform. The computing device may be configured to obtain the brain measurement data, determine, based on the brain measurement data, a graphical emotion symbol representative of a mental state of the user while the user is engaged in the electronic messaging session, and provide the graphical emotion symbol for use during the electronic messaging session.

The embodiments described herein may allow a user to easily, accurately, and effectively use graphical emotion symbols during an electronic messaging session. Moreover, automatic selection and/or generation of a graphical emotion symbol based on a user's measured brain activity may result in the graphical emotion symbol being more objective and/or accurate than conventional manual approaches to selecting and/or generating graphical emotion symbols. The graphical emotion symbol may be provided in substantially real time (e.g., concurrently) while the user in engaged in an electronic messaging session, where the user can convey a current mental state or feeling during the session. These and other benefits are described more fully herein.

Figure 1:
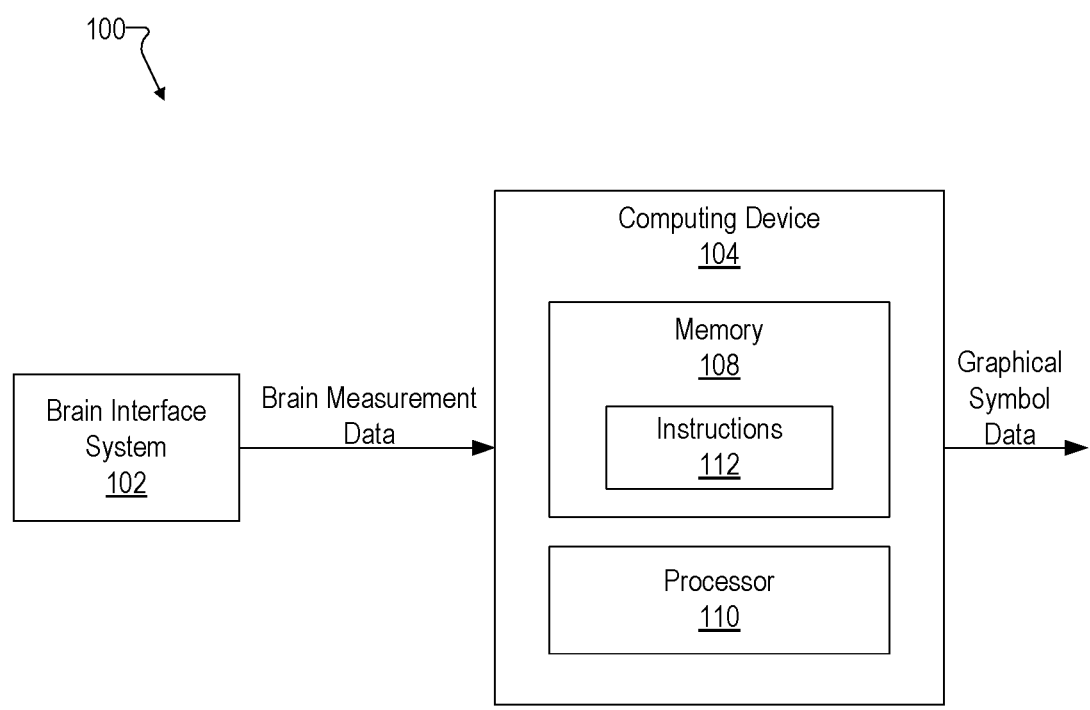
FIG. 1 shows an exemplary configuration that includes a brain interface system and a computing device.

FIG. 1 shows an exemplary configuration 100 that includes a brain interface system 102 and a computing device 104.

Brain interface system 102 may be configured to be worn by a user and to output brain measurement data representative of brain activity of the user while the brain interface system 102 is being worn by the user and while the user is engaged in an electronic messaging session provided by an electronic messaging platform.

As used herein, an electronic messaging session may refer to any time period in which the user is communicating by way of a standalone and/or web-based electronic messaging application executed, for example, by a computing device, a mobile device, a gaming device, an extended reality device, and/or any other electronic device. For example, the electronic messaging application may include a short message service (SMS) (e.g., texting) application, an instant messaging application, an online collaboration application, a video conferencing application, an online chat application, an email application, a social media application, an electronic gaming application, an extended reality application, metaverse application, and/or any other suitable electronic communication application. The electronic messaging platform may include any platform or service that provides, controls, or otherwise manages network resources that facilitate electronic messaging. For example, the electronic messaging platform may be implemented by a social media platform, an online communication platform, an online collaboration platform, an extended reality platform or metaverse platform, and/or any other suitable platform as may serve a particular implementation.

The extended reality experience (e.g., an immersive virtual reality experience or a non-immersive augmented reality experience) may come from virtual reality device, application, or metaverse platform wherein the user or player is engaged virtually to communicate with other users or players. For example, an illustrative system may include an extended reality system and a brain interface system configured to be concurrently worn by a user as described more fully in U.S. patent application Ser. No. 17/466,663, filed Sep. 3, 2021, published as US2022/0091671(A1); and U.S. patent application Ser. No. 17/466,683, filed Sep. 3, 2021, published as US2022/0091672(A1).

As described herein, brain measurement data may include any data output by any of the implementations of brain interface system 102 described herein. For example, the brain measurement data may include or be based on optical-based, electrical-based, and/or magnetic field-based measurements of activity within the brain, as described herein.

Computing device 104 may be configured to obtain (e.g., receive or otherwise access) the brain measurement data. This may be performed in any suitable manner. For example, computing device 104 may receive the brain measurement data from brain interface system 102 by way of a wired and/or wireless (e.g., Bluetooth, WiFi, etc.) connection.

Computing device 104 may be further configured to determine, based on the brain measurement data, a graphical emotion symbol representative of a mental state of the user while the user is engaged in the electronic messaging session.

As used herein, a graphical emotion symbol refers to an emoji, pictogram, logogram, ideogram, emotion-based-pictorial-symbol, and/or any or type of graphic that may be included in an electronic message sent by a user during an electronic messaging session.

As used herein, a mental state may refer to any emotion, reaction, and/or other feeling that a user may have while participating in an electronic messaging session. Example mental states include, but are not limited to, joy, excitement, relaxation, surprise, fear, stress, anxiety, sadness, anger, disgust, contempt, contentment, calmness, approval, focus, attention, creativity, cognitive assessment, positive or negative reflections/attitude on experiences or the use of objects, etc. Further details on the methods and systems related to a predicted brain state, behavior, preferences, or attitude of the user, and the creation, training, and use of neuromes can be found in U.S. patent application Ser. No. 17/188,298, filed Mar. 1, 2021, issued as U.S. Pat. No. 11,132,625. Exemplary measurement systems and methods using biofeedback for awareness and modulation of mental state are described in more detail in U.S. patent application Ser. No. 16/364,338, filed Mar. 26, 2019, issued as U.S. Pat. No. 11,006,876. Exemplary measurement systems and methods used for detecting and modulating the mental state of a user using entertainment selections, e.g., music, film/video, are described in more detail in U.S. patent application Ser. No. 16/835,972, filed Mar. 31, 2020, issued as U.S. Pat. No. 11,006,878. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, issued as U.S. Pat. No. 11,172,869. Exemplary measurement systems and methods used for detecting and modulating the mental state of a user through awareness of priming effects are described in more detail in U.S. patent application Ser. No. 16/885,596, filed May 28, 2020, published as US2020/0390358A1. Exemplary measurement systems and methods used for wellness therapy, such as pain management regime, are described more fully in U.S. Provisional Application No. 63/188,783, filed May 14, 2021. These applications and corresponding U.S. patents and publications are incorporated herein by reference in their entirety.

Computing device 104 may determine a graphical emotion symbol representative of a mental state of the user while the user is engaged in a electronic messaging session in any suitable manner. For example, computing device 104 may determine the graphical emotion symbol by selecting the graphical emotion symbol from a library of graphical emotion symbols and/or generate the graphical emotion symbol. These and other examples are described in more detail herein. In some examples, as shown, computing device 104 may generate graphical emotion symbol data representative of the determined graphical emotion symbol.

Computing device 104 may be further configured to provide the graphical emotion symbol for use during the electronic messaging session. This may be performed in any suitable manner, examples of which are described herein.

Computing device 104 may be implemented by one or more computing or processing devices, such as one or more personal computers, mobile devices (e.g., a mobile phone, a tablet computer, etc.), servers, and/or any other type of computing device as may serve a particular implementation. In some examples, computing device 104 may be included in brain interface system 102. Additionally or alternatively, computing device 104 may be separate from (i.e., remote from and communicatively coupled to) brain interface system 102.

As shown, computing device 104 may include memory 108 and a processor 110. Computing device 104 may include additional or alternative components as may serve a particular implementation. Each component may be implemented by any suitable combination of hardware and/or software.

Memory 108 may maintain (e.g., store) executable data used by processor 110 to perform one or more of the operations described herein as being performed by computing device 104. For example, memory 108 may store instructions 112 that may be executed by processor 110 to generate graphical emotion symbol data. Instructions 112 may be implemented by any suitable application, program, software, code, and/or other executable data instance. Memory 108 may also maintain any data received, generated, managed, used, and/or transmitted by processor 110.

Processor 110 may be configured to perform (e.g., execute instructions 112 stored in memory 108 to perform) various operations described herein as being performed by computing device 104. Examples of such operations are described herein.

In some examples, computing device 104 may obtain the brain measurement data, determine the graphical emotion symbol, and provide the graphical emotion symbol for use during the electronic messaging session in substantially real time while brain interface system 102 outputs the brain measurement data. In this manner, the graphical emotion symbol may be used (e.g., sent to another user) while the user is wearing and using the brain interface system 102.

In another example, the graphical emotion symbol may be used (e.g., sent to another user and/or otherwise provided for use) while the users or players are wearing an extended reality system and a brain interface system configured to be concurrently worn by a user as described more fully in U.S. patent application Ser. No. 17/466,663, filed Sep. 3, 2021, published as US2022/0091671(A1); and U.S. patent application Ser. No. 17/466,683, filed Sep. 3, 2021, published as US2022/0091672(A1).

As used herein, "real time" and "substantially real time" and "concurrently" will be understood to relate to data processing and/or other actions that are performed immediately, as well as conditions and/or circumstances that are accounted for as they exist in the moment, or at the same time, when the processing or other actions are performed. For example, a real-time operation may refer to an operation that is performed immediately and without undue delay, even if it is not possible for there to be absolutely zero delay. Similarly, real-time data, real-time representations, real-time conditions, at the same time conditions, and so forth, will be understood to refer to data, representations, and conditions that relate to a present moment in time or a moment in time when decisions are being made and operations are being performed (e.g., even if after a short delay), such that the data, representations, conditions, and so forth are temporally relevant to the decisions being made and/or the operations being performed.

Brain interface system 102 may be implemented by any suitable wearable non-invasive brain interface system as may serve a particular implementation. For example, brain interface system 102 may be implemented by a wearable optical measurement system configured to perform optical-based brain data acquisition operations, such as any of the wearable optical measurement systems described in U.S. patent application Ser. No. 17/176,315, filed Feb. 16, 2021 and published as US2021/0259638A1; U.S. patent application Ser. No. 17/176,309, filed Feb. 16, 2021 and published as US2021/0259614A1; U.S. patent application Ser. No. 17/176,460, filed Feb. 16, 2021 and issued as U.S. Pat. No. 11,096,620; U.S. patent application Ser. No. 17/176,470, filed Feb. 16, 2021 and published as US2021/0259619A1; U.S. patent application Ser. No. 17/176,487, filed Feb. 16, 2021 and published as US2021/0259632A1; U.S. patent application Ser. No. 17/176,539, filed Feb. 16, 2021 and published as US2021/0259620A1; U.S. patent application Ser. No. 17/176,560, filed Feb. 16, 2021 and published as US2021/0259597A1; U.S. patent application Ser. No. 17/176,466, filed Feb. 16, 2021 and published as US2021/0263320A1; Han Y. Ban, et al., "Kernel Flow: A High Channel Count Scalable TD-fNIRS System," SPIE Photonics West Conference (Mar. 6, 2021); and Han Y. Ban, et al., "Kernel Flow: a high channel count scalable time-domain functional near-infrared spectroscopy system," Journal of Biomedical Optics (Jan. 18, 2022), which applications and publications are incorporated herein by reference in their entirety.

To illustrate, FIGS. 2, 3A, 3B, 4, 5A, and 5B show various optical measurement systems and related components that may implement brain interface system 102. The optical measurement systems described herein are merely illustrative of the many different optical-based brain interface systems that may be used in accordance with the systems and methods described herein.

Figure 2:
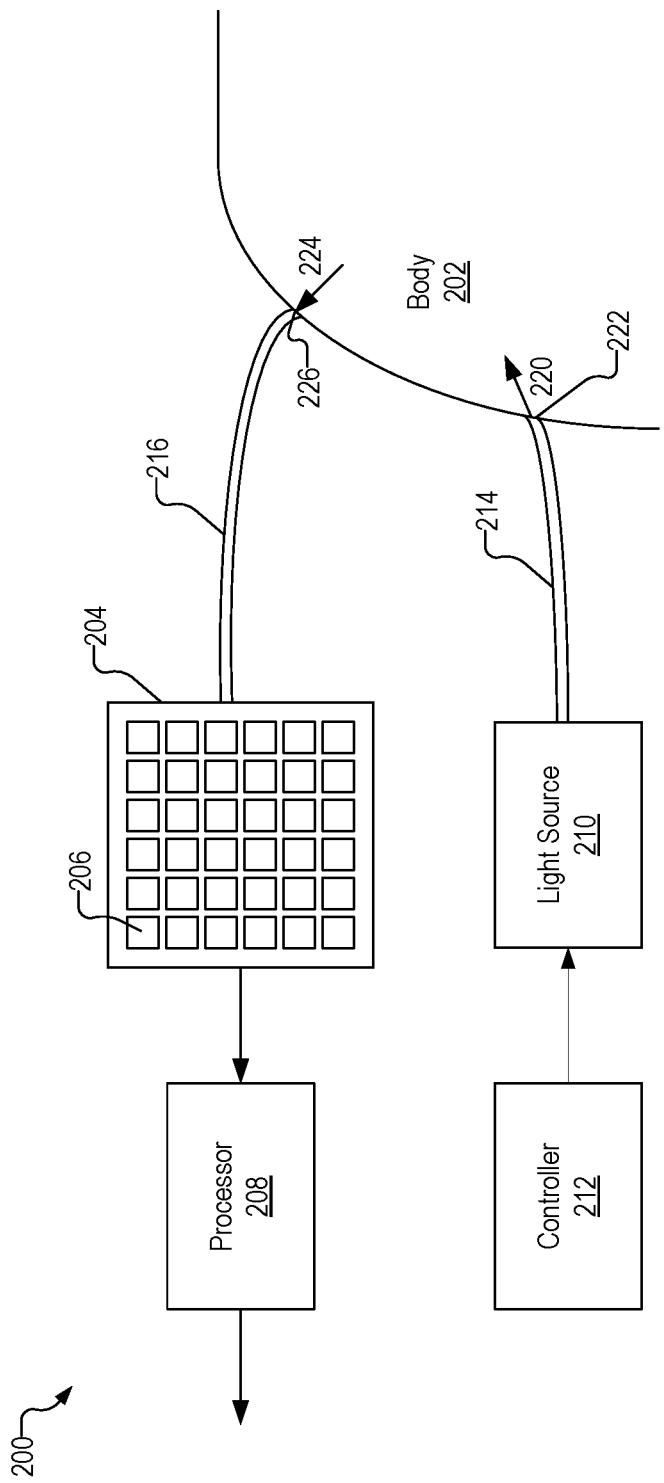
FIGS. 2, 3A, 3B, 4, 5A and 5B show various optical measurement systems that may implement the brain interface system shown in FIG. 1.

FIG. 2 shows an optical measurement system 200 that may be configured to perform an optical measurement operation with respect to a body 202 (e.g., the brain). Optical measurement system 200 may, in some examples, be portable and/or wearable by a user.

In some examples, optical measurement operations performed by optical measurement system 200 are associated with a time domain-based optical measurement technique. Example time domain-based optical measurement techniques include, but are not limited to, time-correlated single-photon counting (TCSPC), time domain near infrared spectroscopy (TD-NIRS), time domain diffusive correlation spectroscopy (TD-DCS), and time domain digital optical tomography (TD-DOT).

Optical measurement system 200 (e.g., an optical measurement system that is implemented by a wearable device or other configuration, and that employs a time domain-based (e.g., TD-NIRS) measurement technique) may detect blood oxygenation levels and/or blood volume levels by measuring the change in shape of laser pulses after they have passed through target tissue, e.g., brain, muscle, finger, etc. As used herein, a shape of laser pulses refers to a temporal shape, as represented for example by a histogram generated by a time-to-digital converter (TDC) coupled to an output of a photodetector, as will be described more fully below.

As shown, optical measurement system 200 includes a detector 204 that includes a plurality of individual photodetectors (e.g., photodetector 206), a processor 208 coupled to detector 204, a light source 210, a controller 212, and optical conduits 214 and 216 (e.g., light pipes). However, one or more of these components may not, in certain embodiments, be considered to be a part of optical measurement system 200. For example, in implementations where optical measurement system 200 is wearable by a user, processor 208 and/or controller 212 may in some embodiments be separate from optical measurement system 200 and not configured to be worn by the user.

Detector 204 may include any number of photodetectors 206 as may serve a particular implementation, such as $2^n$ photodetectors (e.g., 256, 512, . . . , 26384, etc.), where n is an integer greater than or equal to one (e.g., 4, 5, 8, 20, 21, 24, etc.). Photodetectors 206 may be arranged in any suitable manner.

Photodetectors 206 may each be implemented by any suitable circuit configured to detect individual photons of light incident upon photodetectors 206. For example, each photodetector 206 may be implemented by a single photon avalanche diode (SPAD) circuit and/or other circuitry as may serve a particular implementation. The SPAD circuit may be gated in any suitable manner or be configured to operate in a free running mode with passive quenching. For example, photodetectors 206 may be configured to operate in a free-running mode such that photodetectors 206 are not actively armed and disarmed (e.g., at the end of each predetermined gated time window). In contrast, while operating in the free-running mode, photodetectors 206 may be configured to reset within a configurable time period after an occurrence of a photon detection event (i.e., after photodetector 206 detects a photon) and immediately begin detecting new photons. However, only photons detected within a desired time window (e.g., during each gated time window) may be included in the histogram that represents a light pulse response of the target (e.g., a temporal point spread function (TPSF)). The terms histogram and TPSF are used interchangeably herein to refer to a light pulse response of a target.

Processor 208 may be implemented by one or more physical processing (e.g., computing) devices. In some examples, processor 208 may execute instructions (e.g., software) configured to perform one or more of the operations described herein.

Light source 210 may be implemented by any suitable component configured to generate and emit light. For example, light source 210 may be implemented by one or more laser diodes, distributed feedback (DFB) lasers, super luminescent diodes (SLDs), light emitting diodes (LEDs), diode-pumped solid-state (DPSS) lasers, super luminescent light emitting diodes (sLEDs), vertical-cavity surface-emitting lasers (VCSELs), titanium sapphire lasers, micro light emitting diodes (mLEDs), and/or any other suitable laser or light source. In some examples, the light emitted by light source 210 is high coherence light (e.g., light that has a coherence length of at least 5 centimeters) at a predetermined center wavelength.

Light source 210 is controlled by controller 212, which may be implemented by any suitable computing device (e.g., processor 208), integrated circuit, and/or combination of hardware and/or software as may serve a particular implementation. In some examples, controller 212 is configured to control light source 210 by turning light source 210 on and off and/or setting an intensity of light generated by light source 210. Controller 212 may be manually operated by a user, or may be programmed to control light source 210 automatically.

Light emitted by light source 210 may travel via an optical conduit 214 (e.g., a light pipe, a single-mode optical fiber, and/or or a multi-mode optical fiber) to body 202 of a subject. Body 202 may include any suitable turbid medium. For example, in some implementations, body 202 is a brain or any other body part of a human or other animal. Alternatively, body 202 may be a non-living object. For illustrative purposes, it will be assumed in the examples provided herein that body 202 is a human brain.

As indicated by arrow 220, the light emitted by light source 210 enters body 202 at a first location 222 on body 202. Accordingly, a distal end of optical conduit 214 may be positioned at (e.g., right above, in physical contact with, or physically attached to) first location 222 (e.g., to a scalp of the subject). In some examples, the light may emerge from optical conduit 214 and spread out to a certain spot size on body 202 to fall under a predetermined safety limit. At least a portion of the light indicated by arrow 220 may be scattered within body 202.

As used herein, "distal" means nearer, along the optical path of the light emitted by light source 210 or the light received by detector 204, to the target (e.g., within body 202) than to light source 210 or detector 204. Thus, the distal end of optical conduit 214 is nearer to body 202 than to light source 210, and the distal end of optical conduit 216 is nearer to body 202 than to detector 204. Additionally, as used herein, "proximal" means nearer, along the optical path of the light emitted by light source 210 or the light received by detector 204, to light source 210 or detector 204 than to body 202. Thus, the proximal end of optical conduit 214 is nearer to light source 210 than to body 202, and the proximal end of optical conduit 216 is nearer to detector 204 than to body 202.

As shown, the distal end of optical conduit 216 (e.g., a light pipe, a light guide, a waveguide, a single-mode optical fiber, and/or a multi-mode optical fiber) is positioned at (e.g., right above, in physical contact with, or physically attached to) output location 226 on body 202. In this manner, optical conduit 216 may collect at least a portion of the scattered light (indicated as light 224) as it exits body 202 at location 226 and carry light 224 to detector 204. Light 224 may pass through one or more lenses and/or other optical elements (not shown) that direct light 224 onto each of the photodetectors 206 included in detector 204. In cases where optical conduit 216 is implemented by a light guide, the light guide may be spring loaded and/or have a cantilever mechanism to allow for conformably pressing the light guide firmly against body 202.

Photodetectors 206 may be connected in parallel in detector 204. An output of each of photodetectors 206 may be accumulated to generate an accumulated output of detector 204. Processor 208 may receive the accumulated output and determine, based on the accumulated output, a temporal distribution of photons detected by photodetectors 206. Processor 208 may then generate, based on the temporal distribution, a histogram representing a light pulse response of a target (e.g., brain tissue, blood flow, etc.) in body 202. Such a histogram is illustrative of the various types of brain activity measurements that may be performed by brain interface system 102.

Figure 3A:
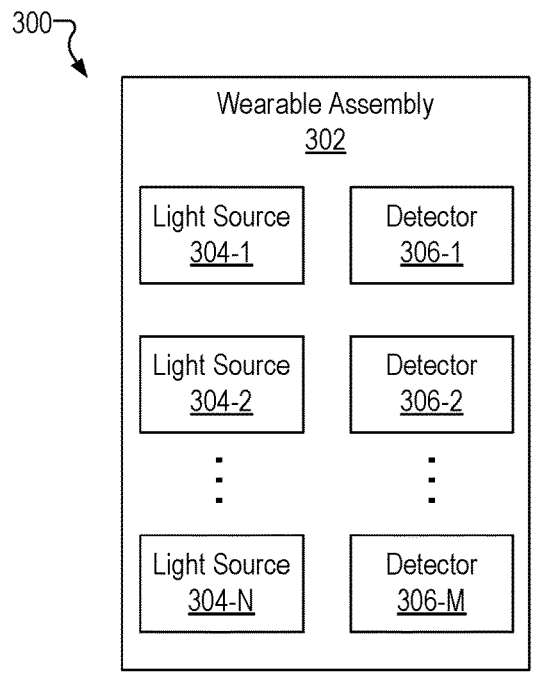
Figure 3B:
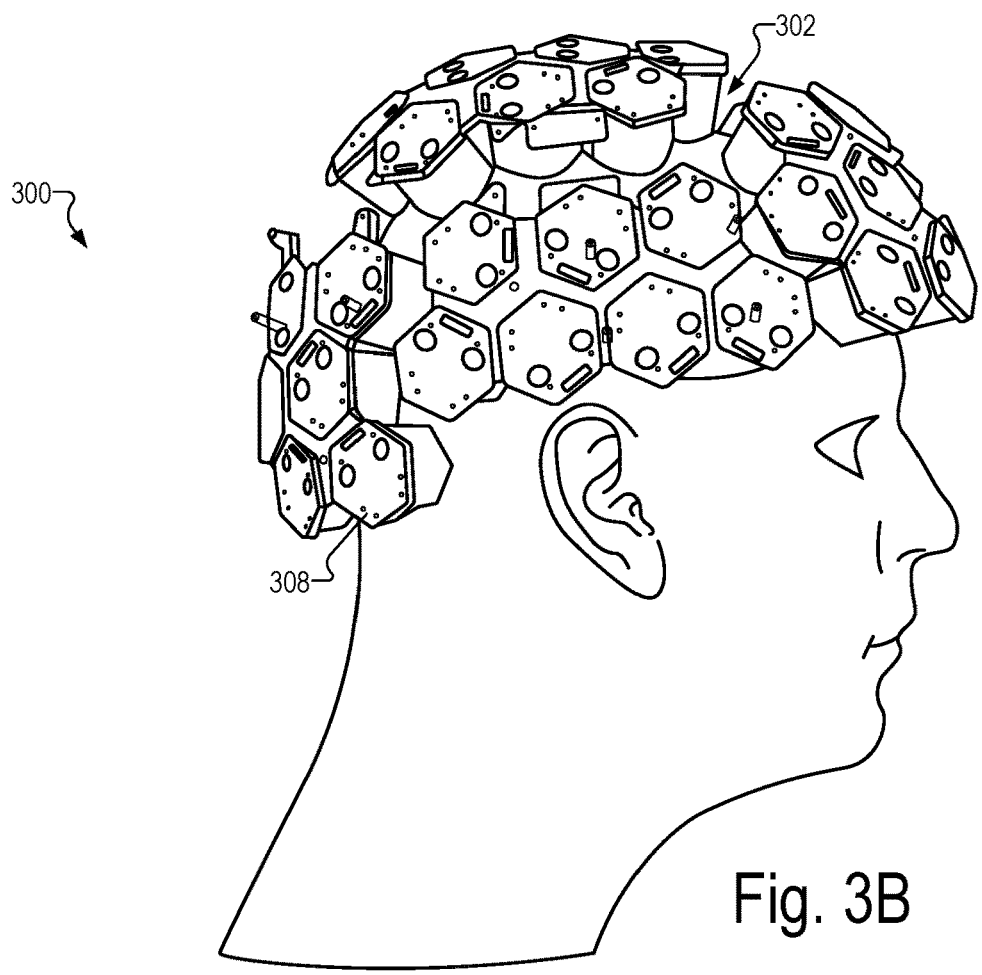

FIGS. 3A and 3B show an exemplary optical measurement system 300 in accordance with the principles described herein. Optical measurement system 300 may be an implementation of optical measurement system 200 and, as shown, includes a wearable assembly 302, which includes N light sources 304 (e.g., light sources 304-1 through 304-N) and M detectors 306 (e.g., detectors 306-1 through 306-M). Optical measurement system 300 may include any of the other components of optical measurement system 200 as may serve a particular implementation. N and M may each be any suitable value (i.e., there may be any number of light sources 304 and detectors 306 included in optical measurement system 300 as may serve a particular implementation).

Light sources 304 are each configured to emit light (e.g., a sequence of light pulses) and may be implemented by any of the light sources described herein. Detectors 306 may each be configured to detect arrival times for photons of the light emitted by one or more light sources 304 after the light is scattered by the target. For example, a detector 306 may include a photodetector configured to generate a photodetector output pulse in response to detecting a photon of the light and a time-to-digital converter (TDC) configured to record a timestamp symbol in response to an occurrence of the photodetector output pulse, the timestamp symbol representative of an arrival time for the photon (i.e., when the photon is detected by the photodetector).

Wearable assembly 302 may be implemented by any of the wearable devices, modular assemblies, and/or wearable units described herein. For example, as shown in FIG. 3B, wearable assembly 302 may be implemented by a wearable device (e.g., headgear) configured to be worn on a user's head. The optical measurement system 300 shown in FIG. 3B may include a plurality of modules 308 arranged in a helmet design. In some examples, modules 308 may be organized on each side of the head, covering the frontal, parietal, temporal, and occipital cortices. Wearable assembly 302 may additionally or alternatively be configured to be worn on any other part of a user's body.

Optical measurement system 300 may be modular in that one or more components of optical measurement system 300 may be removed, changed out, or otherwise modified as may serve a particular implementation. As such, optical measurement system 300 may be configured to conform to three-dimensional surface geometries, such as a user's head (see, for example, FIG. 3B). Exemplary modular optical measurement systems comprising a plurality of wearable modules are described in more detail in U.S. patent application Ser. No. 17/176,460, filed Feb. 16, 2021 and issued as U.S. Pat. No. 11,096,620, U.S. patent application Ser. No. 17/176,470, filed Feb. 16, 2021 and published as US2021/0259619A1, U.S. patent application Ser. No. 17/176,487, filed Feb. 16, 2021 and published as US2021/0259632A1, U.S. patent application Ser. No. 17/176,539, filed Feb. 16, 2021 and published as US2021/0259620A1, U.S. patent application Ser. No. 17/176,560, filed Feb. 16, 2021 and published as US2021/0259597A1, and U.S. patent application Ser. No. 17/176,466, filed Feb. 16, 2021 and published as US2021/0263320A1, which applications are incorporated herein by reference in their respective entireties.

Figure 4:
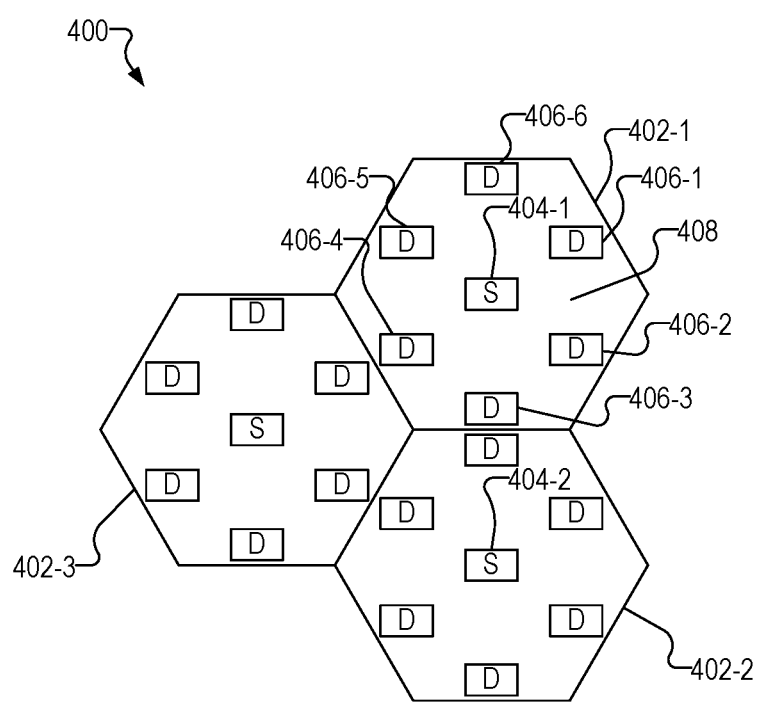

FIG. 4 shows an illustrative modular assembly 400 that may implement optical measurement system 300. Modular assembly 400 is illustrative of the many different implementations of optical measurement system 300 that may be realized in accordance with the principles described herein.

As shown, modular assembly 400 includes a plurality of modules 402 (e.g., modules 402-1 through 402-3) physically distinct one from another. While three modules 402 are shown to be included in modular assembly 400, in alternative configurations, any number of modules 402 (e.g., a single module up to sixteen or more modules) may be included in modular assembly 400.

Each module 402 includes a light source (e.g., light source 404-1 of module 402-1 and light source 404-2 of module 402-2) and a plurality of detectors (e.g., detectors 406-1 through 406-6 of module 402-1). In the particular implementation shown in FIG. 4, each module 402 includes a single light source and six detectors. Each light source is labeled "S" and each detector is labeled "D".

Each light source depicted in FIG. 4 may be implemented by one or more light sources similar to light source 210 and may be configured to emit light directed at a target (e.g., the brain).

Each light source depicted in FIG. 4 may be located at a center region of a surface of the light source's corresponding module. For example, light source 404-1 is located at a center region of a surface 408 of module 402-1. In alternative implementations, a light source of a module may be located away from a center region of the module.

Each detector depicted in FIG. 4 may implement or be similar to detector 204 and may include a plurality of photodetectors (e.g., SPADs) as well as other circuitry (e.g., TDCs), and may be configured to detect arrival times for photons of the light emitted by one or more light sources after the light is scattered by the target.

The detectors of a module may be distributed around the light source of the module. For example, detectors 406 of module 402-1 are distributed around light source 404-1 on surface 408 of module 402-1. In this configuration, detectors 406 may be configured to detect photon arrival times for photons included in light pulses emitted by light source 404-1. In some examples, one or more detectors 406 may be close enough to other light sources to detect photon arrival times for photons included in light pulses emitted by the other light sources. For example, because detector 406-3 is adjacent to module 402-2, detector 406-3 may be configured to detect photon arrival times for photons included in light pulses emitted by light source 404-2 (in addition to detecting photon arrival times for photons included in light pulses emitted by light source 404-1).

In some examples, the detectors of a module may all be equidistant from the light source of the same module. In other words, the spacing between a light source (i.e., a distal end portion of a light source optical conduit) and the detectors (i.e., distal end portions of optical conduits for each detector) are maintained at the same fixed distance on each module to ensure homogeneous coverage over specific areas and to facilitate processing of the detected signals. The fixed spacing also provides consistent spatial (lateral and depth) resolution across the target area of interest, e.g., brain tissue. Moreover, maintaining a known distance between the light source, e.g., light emitter, and the detector allows subsequent processing of the detected signals to infer spatial (e.g., depth localization, inverse modeling) information about the detected signals. Detectors of a module may be alternatively disposed on the module as may serve a particular implementation.

In some examples, modular assembly 400 can conform to a three-dimensional (3D) surface of the human subject's head, maintain tight contact of the detectors with the human subject's head to prevent detection of ambient light, and maintain uniform and fixed spacing between light sources and detectors. The wearable module assemblies may also accommodate a large variety of head sizes, from a young child's head size to an adult head size, and may accommodate a variety of head shapes and underlying cortical morphologies through the conformability and scalability of the wearable module assemblies. These exemplary modular assemblies and systems are described in more detail in U.S. patent application Ser. Nos. 17/176,470; 17/176,487; 17/176,539; 17/176,560; 17/176,460; and Ser. No. 17/176,466, which applications have been previously incorporated herein by reference in their respective entireties.

Figure 5A:
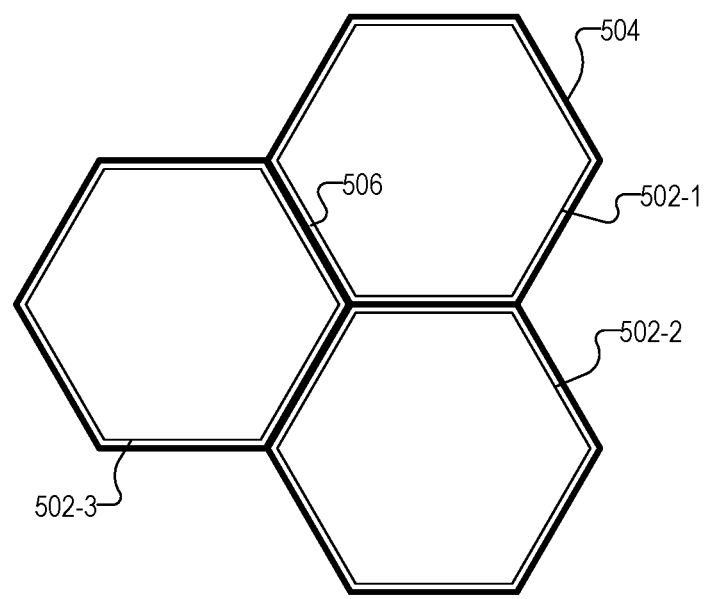
Figure 5B:
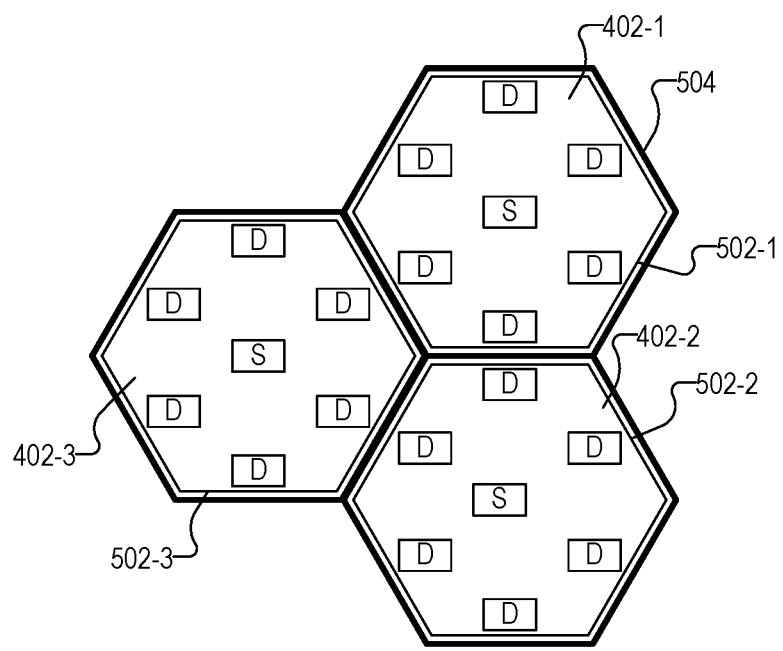

In FIG. 4, modules 402 are shown to be adjacent to and touching one another. Modules 402 may alternatively be spaced apart from one another. For example, FIGS. 5A-5B show an exemplary implementation of modular assembly 400 in which modules 402 are configured to be inserted into individual slots 502 (e.g., slots 502-1 through 502-3, also referred to as cutouts) of a wearable assembly 504. In particular, FIG. 5A shows the individual slots 502 of the wearable assembly 504 before modules 402 have been inserted into respective slots 502, and FIG. 5B shows wearable assembly 504 with individual modules 402 inserted into respective individual slots 502.

Wearable assembly 504 may implement wearable assembly 302 and may be configured as headgear and/or any other type of device configured to be worn by a user.

As shown in FIG. 5A, each slot 502 is surrounded by a wall (e.g., wall 506) such that when modules 402 are inserted into their respective individual slots 502, the walls physically separate modules 402 one from another. In alternative embodiments, a module (e.g., module 402-1) may be in at least partial physical contact with a neighboring module (e.g., module 402-2).

Each of the modules described herein may be inserted into appropriately shaped slots or cutouts of a wearable assembly, as described in connection with FIGS. 5A-5B. However, for ease of explanation, such wearable assemblies are not shown in the figures.

As shown in FIGS. 4 and 5B, modules 402 may have a hexagonal shape. Modules 402 may alternatively have any other suitable geometry (e.g., in the shape of a pentagon, octagon, square, rectangular, circular, triangular, free-form, etc.).

As another example, brain interface system 102 may be implemented by a wearable multimodal measurement system configured to perform both optical-based brain data acquisition operations and electrical-based brain data acquisition operations, such as any of the wearable multimodal measurement systems described in U.S. Patent Application Publication Nos. 2021/0259638 and 2021/0259614, which publications are incorporated herein by reference in their respective entireties.

Figure 6:
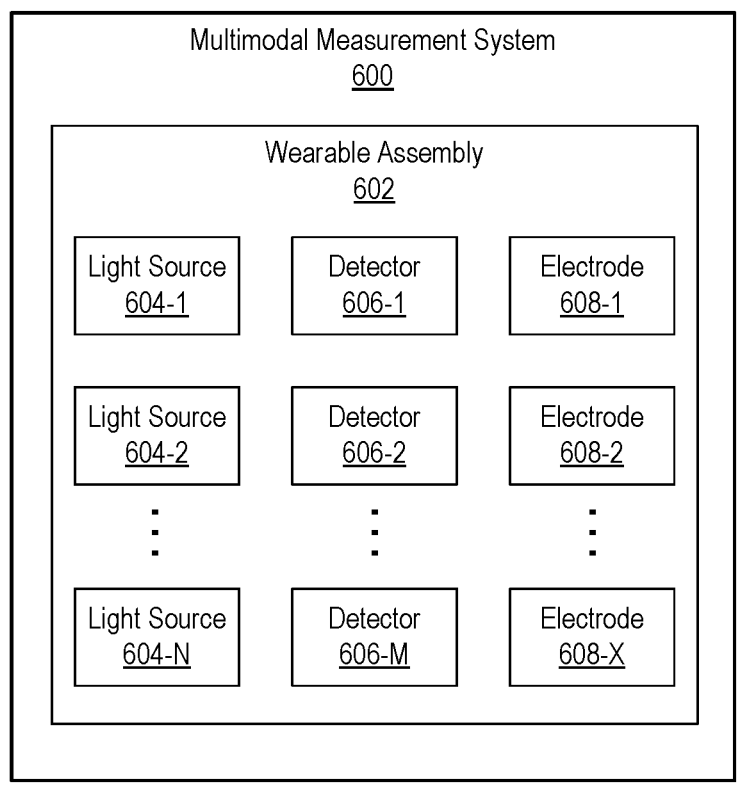
FIGS. 6-7 show various multimodal measurement systems that may implement the brain interface system shown in FIG. 1.
Figure 7:
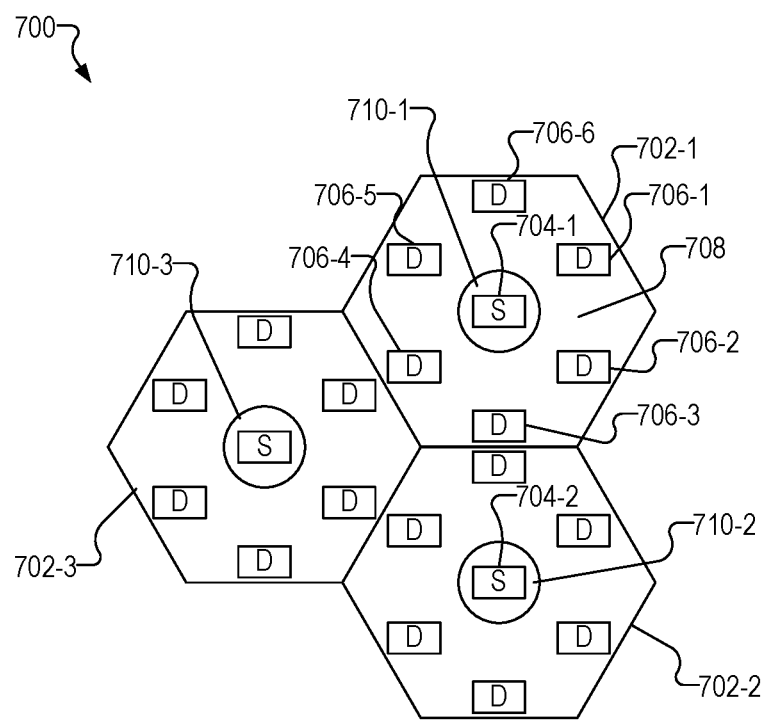

To illustrate, FIGS. 6-7 show various multimodal measurement systems that may implement brain interface system 102. The multimodal measurement systems described herein are merely illustrative of the many different multimodal-based brain interface systems that may be used in accordance with the systems and methods described herein.

FIG. 6 shows an exemplary multimodal measurement system 600 in accordance with the principles described herein. Multimodal measurement system 600 may at least partially implement optical measurement system 200 and, as shown, includes a wearable assembly 602 (which is similar to wearable assembly 302), which includes N light sources 604 (e.g., light sources 604-1 through 604-N, which are similar to light sources 304), M detectors 606 (e.g., detectors 606-1 through 606-M, which are similar to detectors 306), and X electrodes (e.g., electrodes 608-1 through 608-X). Multimodal measurement system 600 may include any of the other components of optical measurement system 200 as may serve a particular implementation. N, M, and X may each be any suitable value (i.e., there may be any number of light sources 604, any number of detectors 606, and any number of electrodes 608 included in multimodal measurement system 600 as may serve a particular implementation).

Electrodes 608 may be configured to detect electrical activity within a target (e.g., the brain). Such electrical activity may include electroencephalogram (EEG) activity and/or any other suitable type of electrical activity as may serve a particular implementation. In some examples, electrodes 608 are all conductively coupled to one another to create a single channel that may be used to detect electrical activity. Alternatively, at least one electrode included in electrodes 608 is conductively isolated from a remaining number of electrodes included in electrodes 608 to create at least two channels that may be used to detect electrical activity.

FIG. 7 shows an illustrative modular assembly 700 that may implement multimodal measurement system 600. As shown, modular assembly 700 includes a plurality of modules 702 (e.g., modules 702-1 through 702-3). While three modules 702 are shown to be included in modular assembly 700, in alternative configurations, any number of modules 702 (e.g., a single module up to sixteen or more modules) may be included in modular assembly 700. Moreover, while each module 702 has a hexagonal shape, modules 702 may alternatively have any other suitable geometry (e.g., in the shape of a pentagon, octagon, square, rectangular, circular, triangular, free-form, etc.).

Each module 702 includes a light source (e.g., light source 704-1 of module 702-1 and light source 704-2 of module 702-2) and a plurality of detectors (e.g., detectors 706-1 through 706-6 of module 702-1). In the particular implementation shown in FIG. 7, each module 702 includes a single light source and six detectors. Alternatively, each module 702 may have any other number of light sources (e.g., two light sources) and any other number of detectors. The various components of modular assembly 700 shown in FIG. 7 are similar to those described in connection with FIG. 4.

As shown, modular assembly 700 further includes a plurality of electrodes 710 (e.g., electrodes 710-1 through 710-3), which may implement electrodes 608. Electrodes 710 may be located at any suitable location that allows electrodes 710 to be in physical contact with a surface (e.g., the scalp and/or skin) of a body of a user. For example, in modular assembly 700, each electrode 710 is on a module surface configured to face a surface of a user's body when modular assembly 700 is worn by the user. To illustrate, electrode 710-1 is on surface 708 of module 702-1. Moreover, in modular assembly 700, electrodes 710 are located in a center region of each module 702 and surround each module's light source 704. Alternative locations and configurations for electrodes 710 are possible.

As another example, brain interface system 102 may be implemented by a wearable magnetic field measurement system configured to perform magnetic field-based brain data acquisition operations, such as any of the magnetic field measurement systems described in U.S. patent application Ser. No. 16/862,879, filed Apr. 30, 2020 and published as US2020/0348368A1; U.S. Provisional Application No. 63/170,892, filed Apr. 5, 2021, U.S. Non-Provisional application Ser. No. 17/338,429, filed Jun. 3, 2021, and Ethan J. Pratt, et al., "Kernel Flux: A Whole-Head 432-Magnetometer Optically-Pumped Magnetoencephalography (OP-MEG) System for Brain Activity Imaging During Natural Human Experiences," SPIE Photonics West Conference (Mar. 6, 2021), which applications and publications are incorporated herein by reference in their entirety. In some examples, any of the magnetic field measurement systems described herein may be used in a magnetically shielded environment which allows for natural user movement as described for example in U.S. Provisional Patent Application No. 63/076,015, filed Sep. 9, 2020, and U.S. Non-Provisional patent application Ser. No. 17/328,235, filed May 24, 2021 and published as US2021/0369166A1, which applications are incorporated herein by reference in their entirety.

Figure 8:
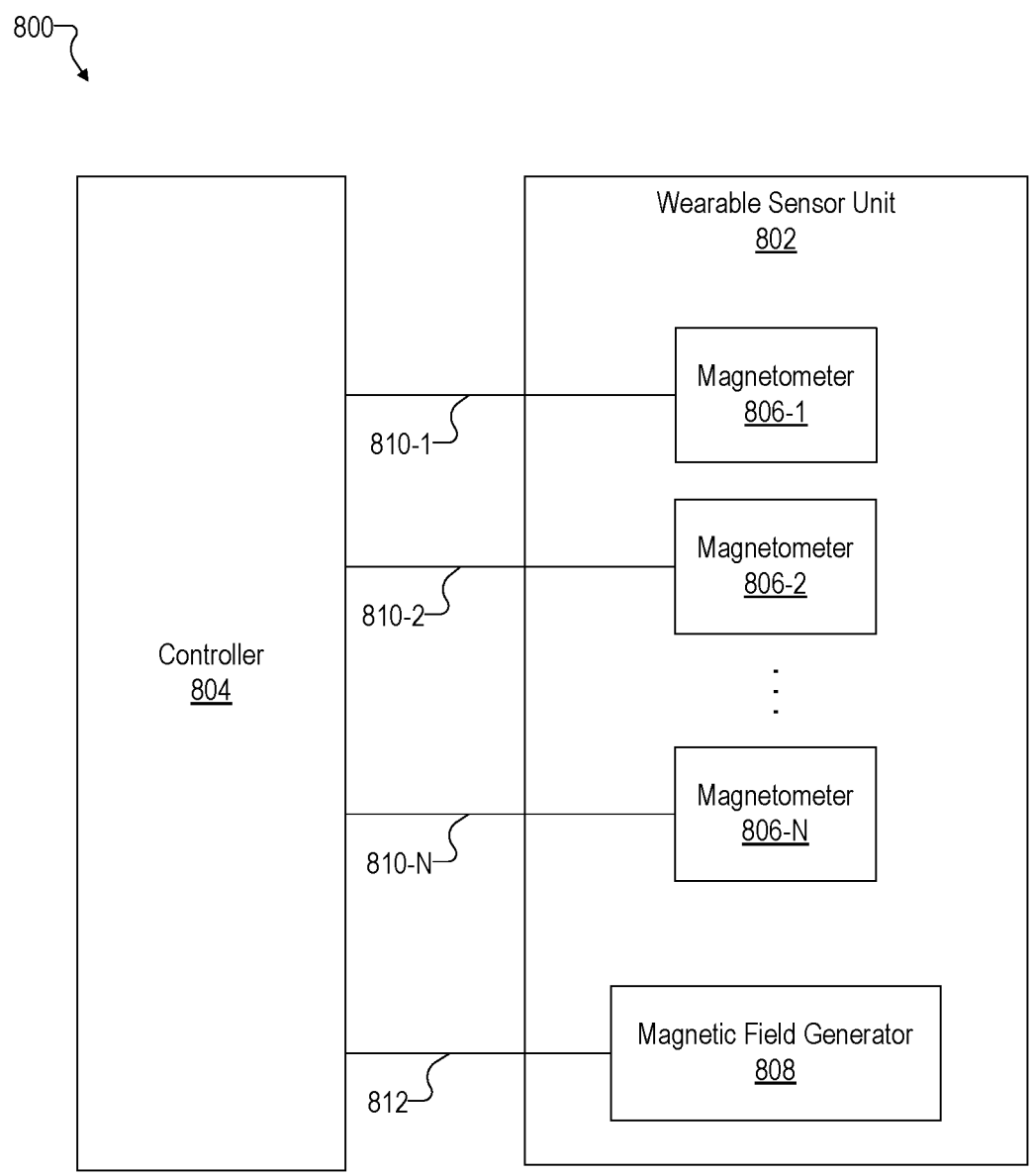
FIG. 8 shows an exemplary magnetic field measurement system that may implement the brain interface system shown in FIG. 1.

FIG. 8 shows an exemplary magnetic field measurement system 800 ("system 800") that may implement brain interface system 102. As shown, system 800 includes a wearable sensor unit 802 and a controller 804. Wearable sensor unit 802 includes a plurality of magnetometers 806-1 through 806-N (collectively "magnetometers 806", also referred to as optically pumped magnetometer (OPM) modular assemblies as described below) and a magnetic field generator 808. Wearable sensor unit 802 may include additional components (e.g., one or more magnetic field sensors, position sensors, orientation sensors, accelerometers, image recorders, detectors, etc.) as may serve a particular implementation. System 800 may be used in magnetoencephalography (MEG) and/or any other application that measures relatively weak magnetic fields.

Wearable sensor unit 802 is configured to be worn by a user (e.g., on a head of the user). In some examples, wearable sensor unit 802 is portable. In other words, wearable sensor unit 802 may be small and light enough to be easily carried by a user and/or worn by the user while the user moves around and/or otherwise performs daily activities, or may be worn in a magnetically shielded environment which allows for natural user movement as described more fully in U.S. Provisional Patent Application No. 63/076,015, and U.S. Non-Provisional patent application Ser. No. 17/328,235, filed May 24, 2021 and published as US2021/0369166A1, previously incorporated by reference.

Any suitable number of magnetometers 806 may be included in wearable sensor unit 802. For example, wearable sensor unit 802 may include an array of nine, sixteen, twenty-five, or any other suitable plurality of magnetometers 806 as may serve a particular implementation.

Magnetometers 806 may each be implemented by any suitable combination of components configured to be sensitive enough to detect a relatively weak magnetic field (e.g., magnetic fields that come from the brain). For example, each magnetometer may include a light source, a vapor cell such as an alkali metal vapor cell (the terms "cell", "gas cell", "vapor cell", and "vapor gas cell" are used interchangeably herein), a heater for the vapor cell, and a photodetector (e.g., a signal photodiode). Examples of suitable light sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source. In some embodiments, the light source may include two light sources: a pump light source and a probe light source.

Magnetic field generator 808 may be implemented by one or more components configured to generate one or more compensation magnetic fields that actively shield magnetometers 806 (including respective vapor cells) from ambient background magnetic fields (e.g., the Earth's magnetic field, magnetic fields generated by nearby magnetic objects such as passing vehicles, electrical devices and/or other field generators within an environment of magnetometers 806, and/or magnetic fields generated by other external sources). For example, magnetic field generator 808 may include one or more coils configured to generate compensation magnetic fields in the Z direction, X direction, and/or Y direction (all directions are with respect to one or more planes within which the magnetic field generator 808 is located). The compensation magnetic fields are configured to cancel out, or substantially reduce, ambient background magnetic fields in a magnetic field sensing region with minimal spatial variability.

Controller 804 is configured to interface with (e.g., control an operation of, receive signals from, etc.) magnetometers 806 and the magnetic field generator 808. Controller 804 may also interface with other components that may be included in wearable sensor unit 802.

In some examples, controller 804 is referred to herein as a "single" controller 804. This means that only one controller is used to interface with all of the components of wearable sensor unit 802. For example, controller 804 may be the only controller that interfaces with magnetometers 806 and magnetic field generator 808. It will be recognized, however, that any number of controllers may interface with components of magnetic field measurement system 800 as may suit a particular implementation.

As shown, controller 804 may be communicatively coupled to each of magnetometers 806 and magnetic field generator 808. For example, FIG. 8 shows that controller 804 is communicatively coupled to magnetometer 806-1 by way of communication link 810-1, to magnetometer 806-2 by way of communication link 810-2, to magnetometer 806-N by way of communication link 810-N, and to magnetic field generator 808 by way of communication link 812. In this configuration, controller 804 may interface with magnetometers 806 by way of communication links 810-1 through 810-N (collectively "communication links 810") and with magnetic field generator 808 by way of communication link 812.

Communication links 810 and communication link 812 may be implemented by any suitable wired connection as may serve a particular implementation. For example, communication links 810 may be implemented by one or more twisted pair cables while communication link 812 may be implemented by one or more coaxial cables. Alternatively, communication links 810 and communication link 812 may both be implemented by one or more twisted pair cables. In some examples, the twisted pair cables may be unshielded.

Controller 804 may be implemented in any suitable manner. For example, controller 804 may be implemented by a field-programmable gate array (FPGA), an application specific integrated circuit (ASIC), a digital signal processor (DSP), a microcontroller, and/or other suitable circuit together with various control circuitry.

In some examples, controller 804 is implemented on one or more printed circuit boards (PCBs) included in a single housing. In cases where controller 804 is implemented on a PCB, the PCB may include various connection interfaces configured to facilitate communication links 810 and 812. For example, the PCB may include one or more twisted pair cable connection interfaces to which one or more twisted pair cables may be connected (e.g., plugged into) and/or one or more coaxial cable connection interfaces to which one or more coaxial cables may be connected (e.g., plugged into).

In some examples, controller 804 may be implemented by or within a computing device.

In some examples, a wearable magnetic field measurement system may include a plurality of optically pumped magnetometer (OPM) modular assemblies, which OPM modular assemblies are enclosed within a housing sized to fit into a headgear (e.g., brain interface system 102) for placement on a head of a user (e.g., human subject). The OPM modular assembly is designed to enclose the elements of the OPM optics, vapor cell, and detectors in a compact arrangement that can be positioned close to the head of the human subject. The headgear may include an adjustment mechanism used for adjusting the headgear to conform with the human subject's head. These exemplary OPM modular assemblies and systems are described in more detail in U.S. Provisional Patent Application No. 63/170,892 filed Apr. 5, 2021, and U.S. Non-Provisional application Ser. No. 17/338,429, filed Jun. 3, 2021, previously incorporated by reference.

At least some of the elements of the OPM modular assemblies, systems which can employ the OPM modular assemblies, and methods of making and using the OPM modular assemblies have been disclosed in U.S. Patent Application Publications Nos. 2020/0072916; 2020/0056263; 2020/0025844; 2020/0057116; 2019/0391213; 2020/0088811; 2020/0057115; 2020/0109481; 2020/0123416; 2020/0191883; 2020/0241094; 2020/0256929; 2020/0309873; 2020/0334559; 2020/0341081; 2020/0381128; 2020/0400763; 2021/0011094; 2021/0015385; 2021/0041512; 2021/0041513; 2021/0063510; and 2021/0139742, and U.S. Provisional Patent Application Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032; 62/926,043; 62/933,085; 62/960,548; 62/971,132; 63/031,469; 63/052,327; 63/076,015; 63/076,880; 63/080,248; 63/135,364; 63/136,415; and 63/170,892, all of which are incorporated herein by reference in their entireties.

In some examples, one or more components of brain interface system 102, FIG. 1, (e.g., one or more computing devices) may be configured to be located off the head of the user.

In each of the different brain interface system implementations described herein, the brain measurement data may be based on the type of operations performed by the different brain interface system implementations. For example, if brain interface system 102 is implemented by an optical measurement system configured to perform optical-based brain data acquisition operations, the brain measurement data may be based on the optical-based brain data acquisition operations. As another example, if brain interface system 102 is implemented by a multimodal measurement system configured to perform optical-based brain data acquisition operations and electrical-based brain data acquisition operations, the brain measurement data may be based on the optical-based brain data acquisition operations and the electrical-based brain data acquisition operations. As another example, if brain interface system 102 is implemented by a magnetic field measurement system configured to perform magnetic field-based brain data acquisition operations, the brain measurement data may be based on the magnetic field-based brain data acquisition operations.

Figure 9:
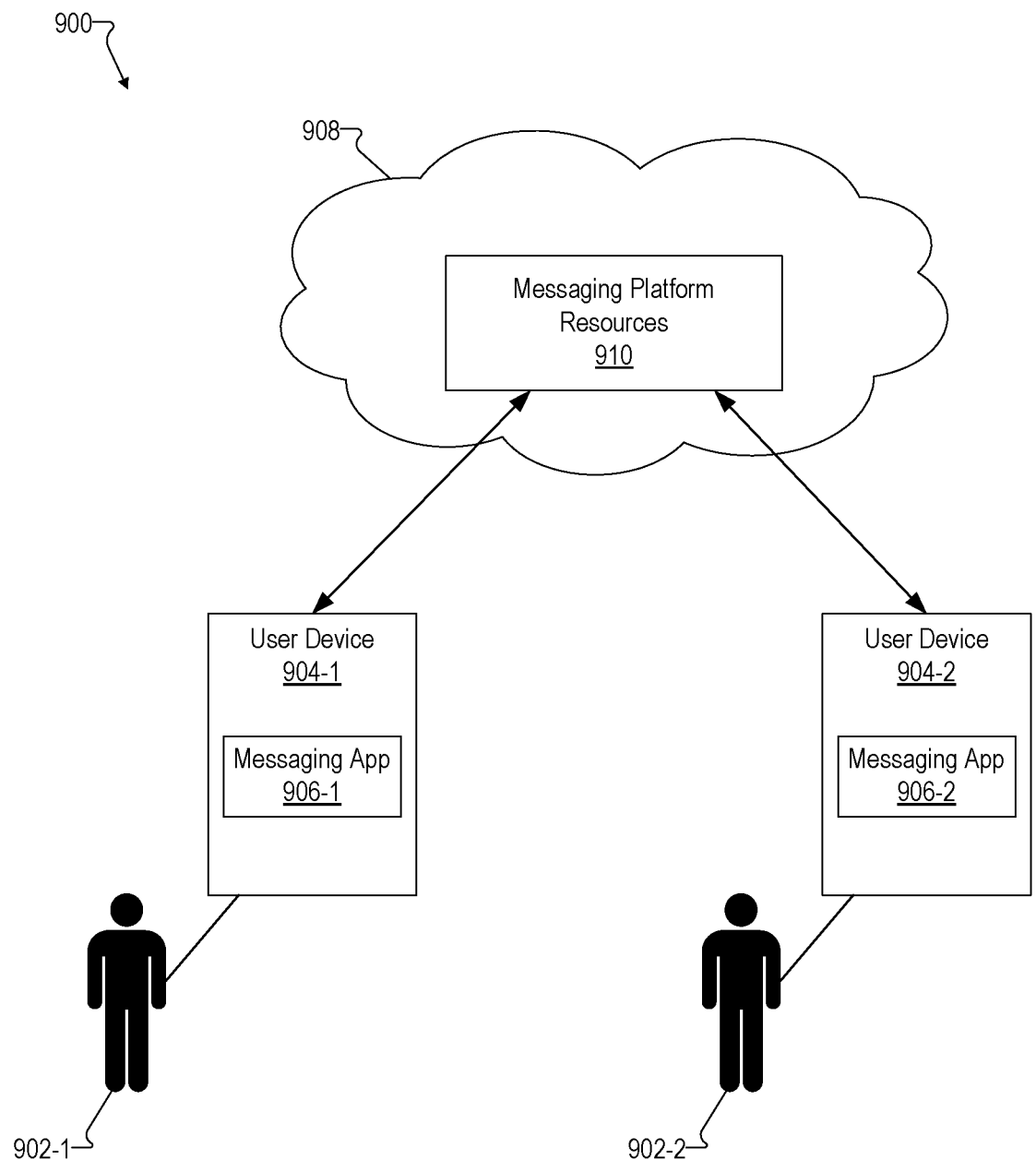
FIG. 9 shows an exemplary implementation of an electronic messaging platform configured to provide an electronic messaging service for a plurality of users.

FIG. 9 shows an exemplary implementation 900 of an electronic messaging platform configured to provide an electronic messaging service for a plurality of users 902 (e.g., user 902-1 and user 902-2). As shown, each user 902 may use a user device 904 (e.g., user device 904-1 and user device 904-2) to access a messaging application 906 (e.g., messaging application 906-1 and messaging application 906-2). User devices 904 may be implemented by any suitable computing device configured to connect to a network 908 (e.g., the Internet and/or any other suitable network). Messaging applications 906 may be provided by or otherwise associated with an electronic messaging service provided by an electronic messaging platform.

As shown, network-based messaging platform resources 910 may be configured to facilitate communication between user devices 904 (e.g., by way of messaging applications 906). Messaging platform resources 910 may include any suitable computing resources, such as servers, network equipment, and/or other computing devices configured to provide the electronic messaging platform. In some examples, computing device 104 is implemented by messaging platform resources 910, user devices 904, and/or any other computing device as may serve a particular implementation.

In some examples, one or both of users 902 may wear a brain interface system (e.g., brain interface system 102) while they participate in an electronic messaging session by way of messaging applications 906. For illustrative purposes, it will be assumed that user 902-1 wears brain interface system 102 while participating in the electronic messaging session. As such, computing device 104 may be configured to determine a graphical emotion symbol representative of a mental state of user 902-1 based on brain measurement data output by brain interface system 102 and provide the graphical emotion symbol (e.g., in real time) for use during the electronic messaging session. Examples of this are described herein.

Computing device 104 may determine a graphical emotion symbol representative of a mental state of a user based on brain measurement data output by brain interface system 102 in any suitable manner.

For example, computing device 104 may determine, based on the brain measurement data, a mental state of the user and automatically select, from a library of graphical emotion symbols, a graphical emotion symbol that is associated with the mental state. For example, the electronic messaging platform and/or computing device 104 may maintain a library of graphical emotion symbols and correlation data indicating a relationship between each of the graphical emotion symbols and one or more mental states. Accordingly, once the mental state of the user is determined, computing device 104 may use any selection algorithm to select a graphical emotion symbol that includes correlation data that most closely matches the determined mental state.

As another example, computing device 104 may determine, based on the brain measurement data, a mental state of the user and generate a custom graphical emotion symbol representative of the mental state. For example, computing device 104 may be configured to draw, in accordance with one or more preferences set by the user, a custom graphical emotion symbol representative of the mental state.

In some examples, the determination of the graphical emotion symbol may be further based on one or more characteristics of the user. For example, computing device 104 may access user profile data for the user, which may indicate an age, gender, user defined preferences for graphical emotion symbols, historical graphical emotion symbol usage of the user, and/or one or more other traits of the user. The user profile data may be used to further customize the graphical emotion symbol selected and/or generated by computing device 104.

In some examples, brain interface system 102 may be configured to output baseline brain measurement data while the user is not engaged in the electronic messaging session. Computing device 104 may obtain the baseline brain measurement data, compare the brain measurement data with the baseline brain measurement data, and then base the determination of the graphical emotion symbol on the comparison. In some examples, the baseline measurement of brain activity can provide a more accurate assessment on the user's neurons being flared by current state of multiple emotions, which emotions may be flared by the communication stimuli before and during the electronic messaging session, thereby promoting more objective, and thus, a more accurate emotional status. Using a wearable brain interface for emotional characterization may thereby provide graphical emotion symbols tailored to each user, without requiring subjective input from the user.

Figure 10:
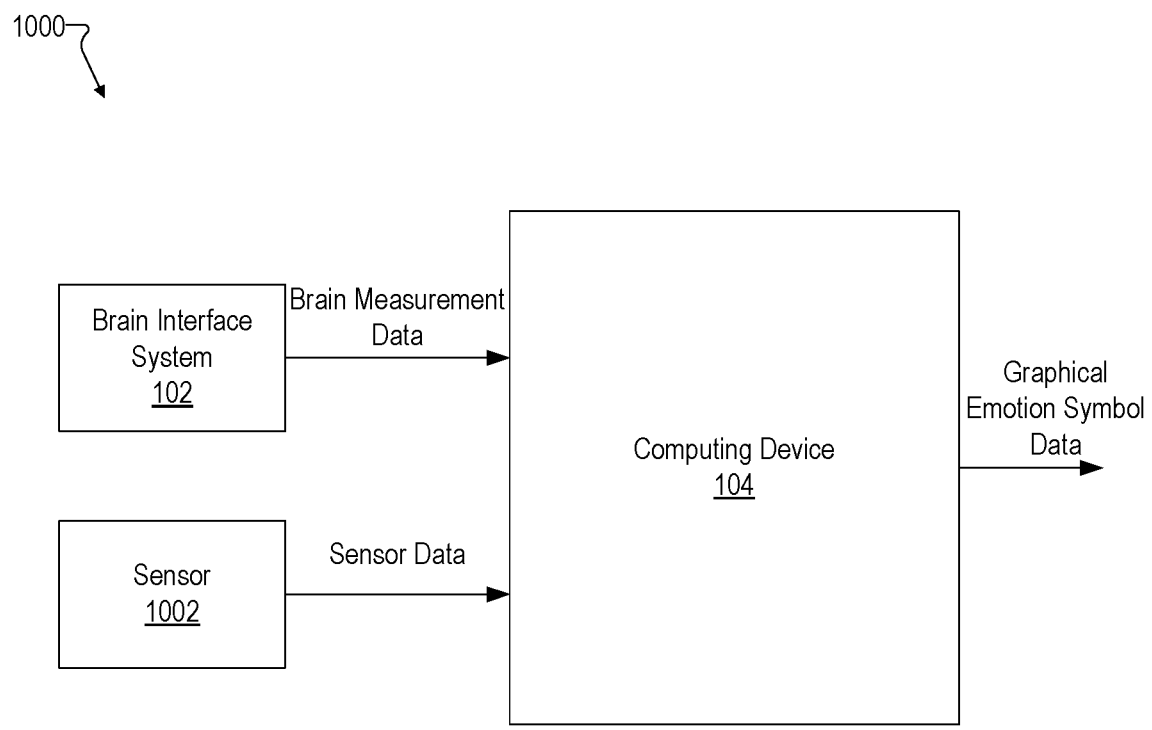
FIG. 10 shows an illustrative configuration in which a computing device is configured to access both brain measurement data and sensor data output by a sensor.

FIG. 10 shows an illustrative configuration 1000 in which computing device 104 is configured to access both brain measurement data and sensor data output by a sensor 1002. The sensor data may be representative of a sensed attribute of the user. In this example, computing device 104 may be configured to determine the graphical emotion symbol data based on both the brain measurement data and the sensor data.

Sensor 1002 may be implemented in any suitable manner. For example, sensor 1002 may be implemented by one or more sensors that perform eye tracking, electrodermal activity (EDA)/conductance, pupillometry, heart rate, heart rate variability, and/or pulse oximetry. Additionally or alternatively, sensor 1002 may be implemented by one or more microphones configured to detect ambient sound of the user, one or more inertial motion units (IMUs) configured to detect movement by the user, etc. In some examples, the sensor data may be presented within a graphical user interface. An example of this is described in U.S. patent application Ser. No. 17/550,387, filed Dec. 14, 2021 and incorporated herein by reference in its entirety.

Computing device 104 may use any suitable statistical analysis and/or or other data processing technique to transform the brain measurement data into graphical emotion symbol data representative of the graphical emotion symbol.

Figure 11:
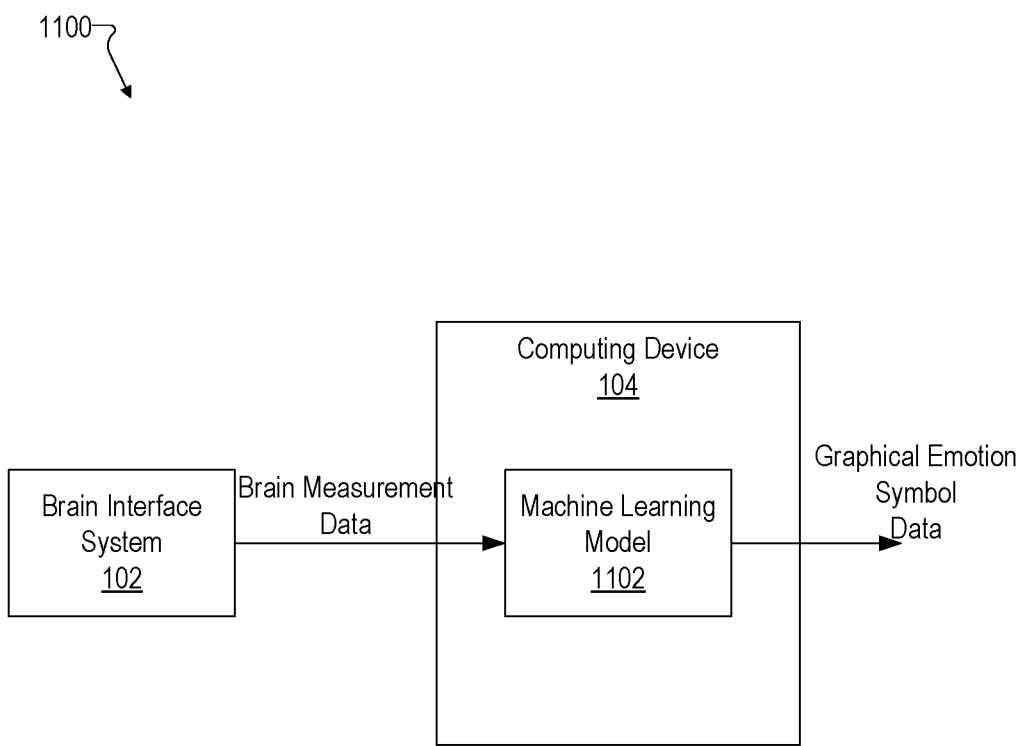
FIG. 11 shows an illustrative configuration in which a computing device is configured to implement a machine learning model to generate graphical emotion symbol data.

For example, computing device 104 may use a machine learning model to generate the graphical emotion symbol data. FIG. 11 shows an illustrative configuration 1100 in which computing device 104 is configured to implement a machine learning model 1102 to generate the graphical emotion symbol data.

Machine learning model 1102 may be configured to perform any suitable machine learning heuristic (also referred to as artificial intelligence heuristic) to input data, which may be in either the time or frequency domains.

Machine learning model 1102 may accordingly be supervised and/or unsupervised as may serve a particular implementation and may be configured to implement one or more decision tree learning algorithms, association rule learning algorithms, artificial neural network learning algorithms, deep learning algorithms, bitmap algorithms, and/or any other suitable data analysis technique as may serve a particular implementation.

In some examples, machine learning model 1102 is implemented by one or more neural networks, such as one or more deep convolutional neural networks (CNN) using internal memories of its respective kernels (filters), recurrent neural networks (RNN), and/or long/short term memory neural networks (LSTM). Machine learning model 1102 may be multi-layer. For example, machine learning model 1102 may be implemented by a neural network that includes an input layer, one or more hidden layers, and an output layer. Machine learning model 1102 may be trained in any suitable manner.

Computing device 104 may provide a graphical emotion symbol for use during an electronic messaging session in any suitable manner. For example, computing device 104 may include the graphical emotion symbol in an electronic message sent by the user to an additional user by way of the electronic messaging platform.

Figure 12:
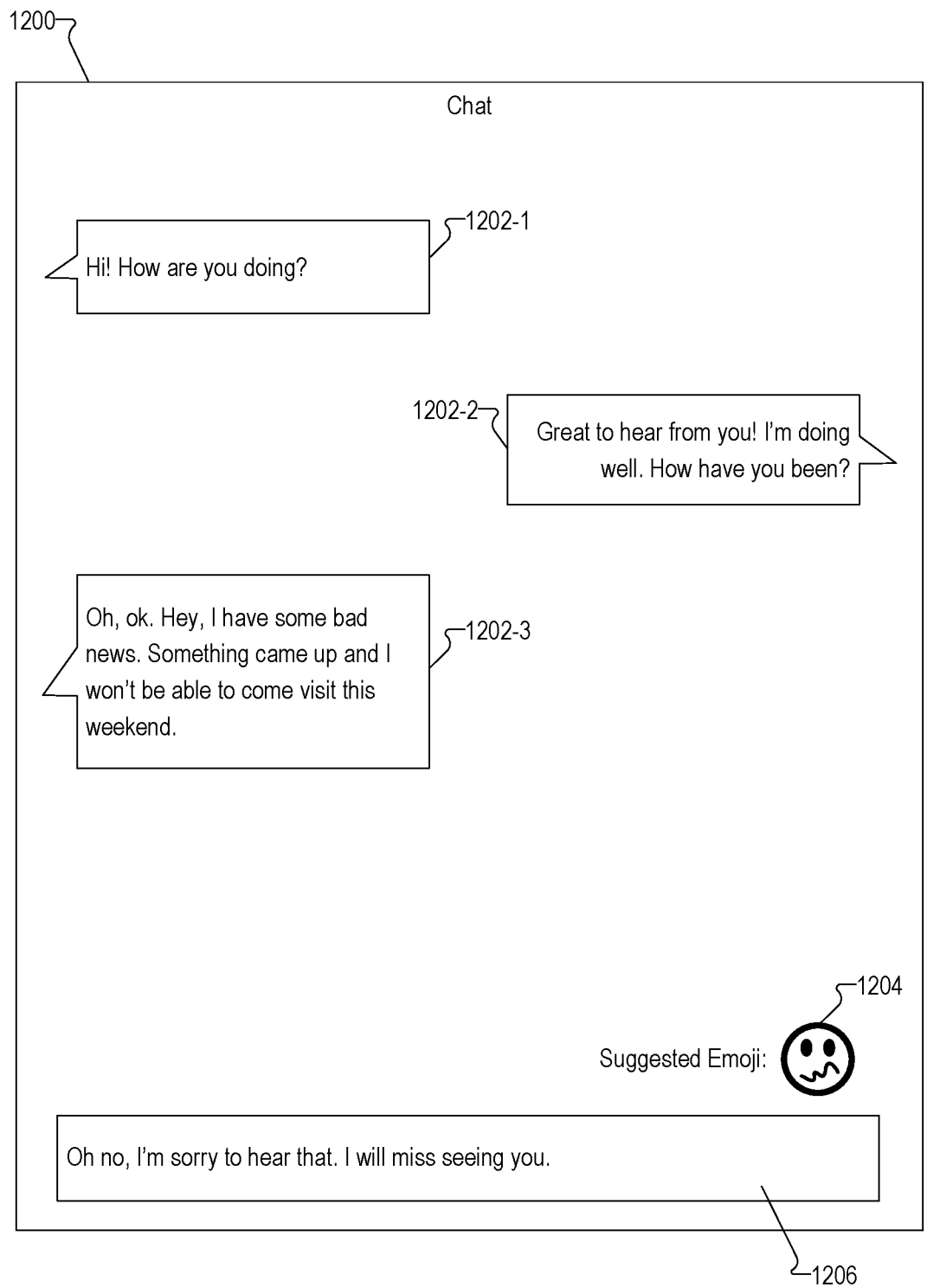
FIGS. 12-14 illustrate example graphical user interfaces.

To illustrate, reference is again made to the configuration shown in FIG. 9 in which user 902-1 wears brain interface system 102 while engaging in an electronic messaging session with user 902-2 by way of messaging applications 906. FIG. 12 shows an example graphical user interface 1200 that may be presented by user device 904-1 while user 902-1 is engaged in the electronic messaging session. As show, user 902-2 initially sends a first message 1202-1: "Hi! How are you doing?". User 902-1 replies with a second message 1202-2: "Great to hear from you! I'm doing well. How have you been?". In response, user 902-2 sends message 1202-3: "Oh, ok. Hey, I have some bad news. Something came up and I won't be able to come visit this weekend."

Figure 13:
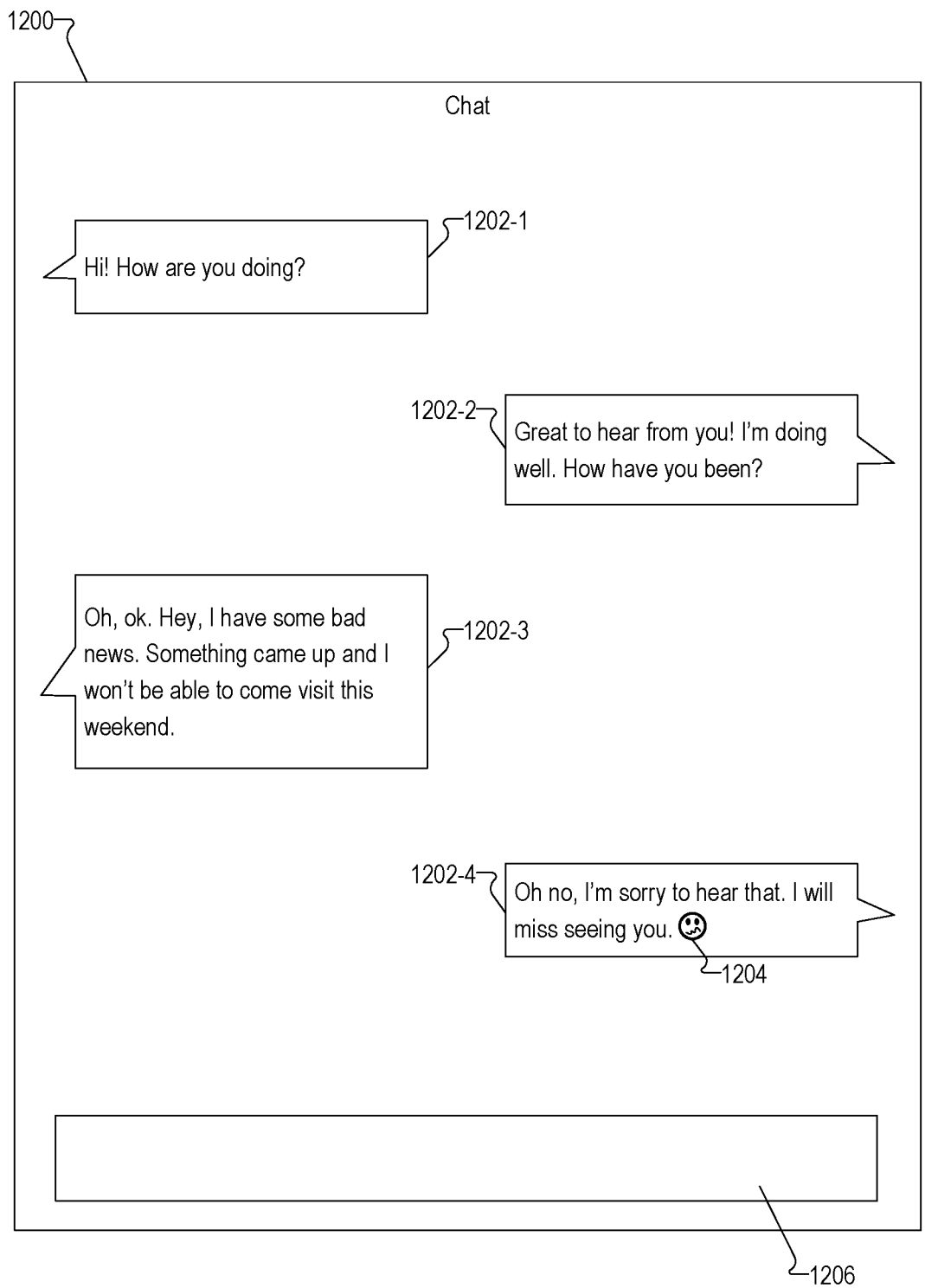

At this point, the brain measurement data of user 902-1 may indicate that user 902-1 feels a mix of sadness and anxiety upon learning that user 902-2 will not be able to visit. Accordingly, computing device 104 may select and/or generate a graphical emotion symbol 1204, which represents this combination of sadness and anxiety. Computing device 104 may present graphical emotion symbol 1204 as an option for user 902-1 to include in a new message that the user is composing in text input box 1206. User 902-1 may select the graphical emotion symbol 1204 for inclusion in the new message in any suitable manner (e.g., by touching the graphical emotion symbol 1204 via touch screen functionality or mouse curser functionality). FIG. 13 shows graphical user interface 1200 after user 902-1 has included graphical emotion symbol 1204 in the new message 1204-4 and sent the new message 1204-4 to user 902-2.

Figure 14:
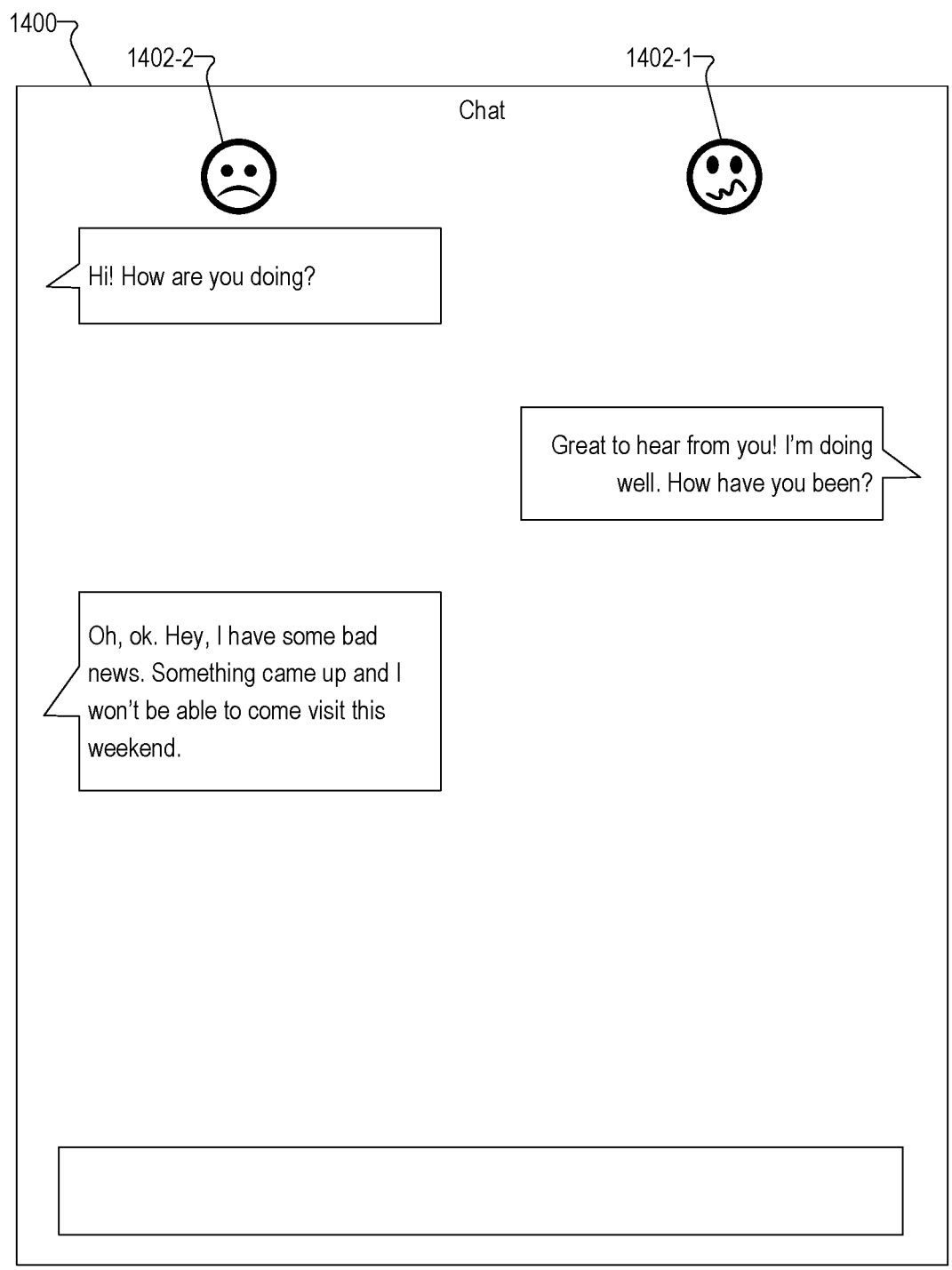

FIG. 14 shows another example graphical user interface 1400 that may be presented by user device 904-1 while user 902-1 is engaged in the electronic messaging session with user 902-2. In this example, both users 902 are wearing brain interface systems during the electronic messaging session. In this manner, graphical emotion symbols for both users 902 may be automatically selected and/or generated. For example, graphical emotion symbol 1402-1 may be automatically selected and/or generated for user 902-1 and graphical emotion symbol 1402-2 may be automatically selected and/or generated for user 902-2. As shown, graphical emotion symbols 1402 may be presented within graphical user interface 1400 (e.g., automatically without being manually selected by either user 902) so that user 902-1 may readily ascertain both users' mental states in real time as the conversation progresses. In some examples, a similar graphical user interface may be presented by user device 904-2 so that user 902-2 may likewise ascertain both users' mental states.

In some examples, computing device 104 may be additionally or alternatively configured to present, by way of a graphical user interface, content representative of the brain measurement data to the user. This is described in more detail in U.S. patent application Ser. No. 17/559,316, filed Dec. 22, 2021, and incorporated herein by reference in its entirety.

Figure 15:
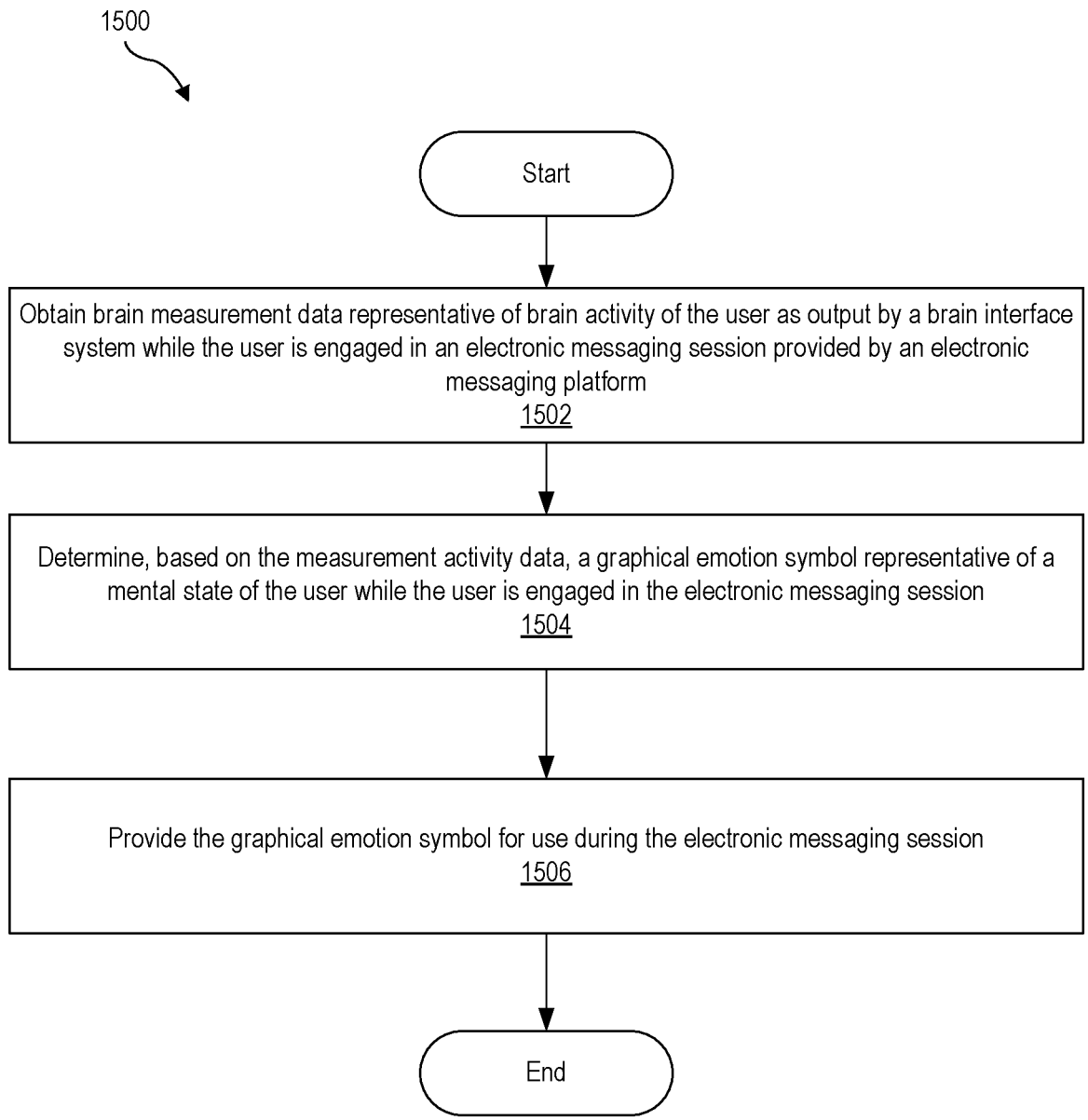
FIG. 15 illustrates an exemplary method.

FIG. 15 illustrates an exemplary method 1500. While FIG. 15 illustrates exemplary operations according to one embodiment, other embodiments may omit, add to, reorder, and/or modify any of the operations shown in FIG. 15. One or more of the operations shown in FIG. 15 may be performed by computing device 104 and/or any implementation thereof. Each of the operations illustrated in FIG. 15 may be performed in any suitable manner.

At operation 1502, a computing device may obtain brain measurement data representative of brain activity of the user as output by a brain interface system while the user is engaged in an electronic messaging session provided by an electronic messaging platform.

At operation 1504, the computing device may determine, based on the brain measurement data, a graphical emotion symbol representative of a mental state of the user while the user is engaged in the electronic messaging session.

At operation 1506, the computing device may provide the graphical emotion symbol for use (e.g, in real time) during the electronic messaging session.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 16:
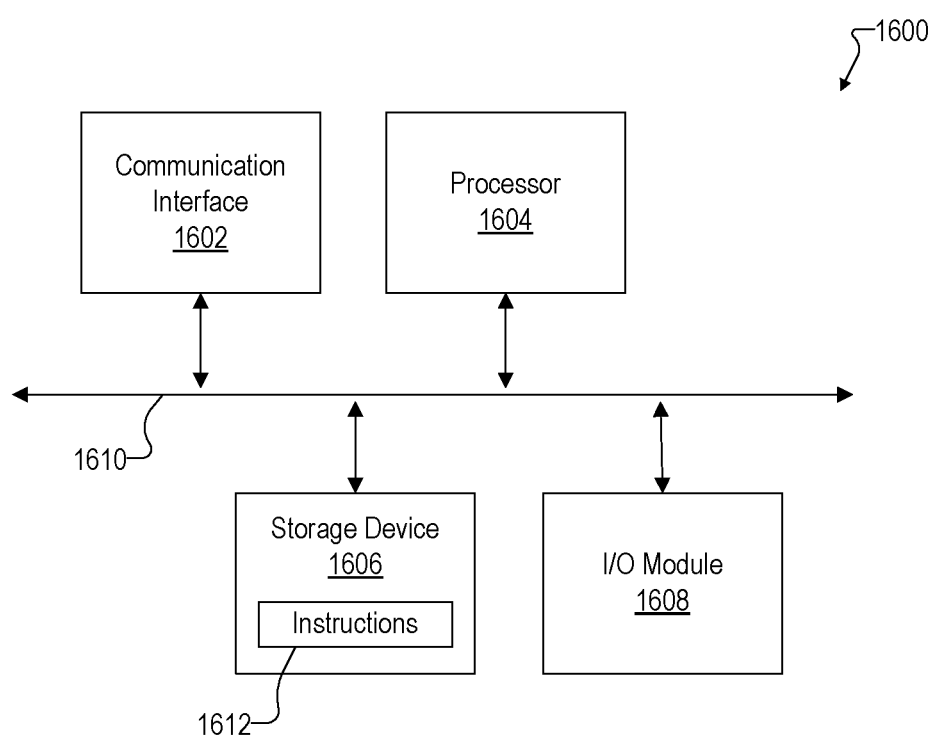
FIG. 16 illustrates an exemplary computing device.

FIG. 16 illustrates an exemplary computing device 1600 that may be specifically configured to perform one or more of the processes described herein. Any of the systems, units, computing devices, and/or other components described herein may be implemented by computing device 1600.

As shown in FIG. 16, computing device 1600 may include a communication interface 1602, a processor 1604, a storage device 1606, and an input/output ("I/O") module 1608 communicatively connected one to another via a communication infrastructure 1610. While an exemplary computing device 1600 is shown in FIG. 16, the components illustrated in FIG. 16 are not intended to be limiting. Additional or alternative components may be used in other embodiments. Components of computing device 1600 shown in FIG. 16 will now be described in additional detail.

Communication interface 1602 may be configured to communicate with one or more computing devices. Examples of communication interface 1602 include, without limitation, a wired network interface (such as a network interface card), a wireless network interface (such as a wireless network interface card), a modem, an audio/video connection, and any other suitable interface.

Processor 1604 generally represents any type or form of processing unit capable of processing data and/or interpreting, executing, and/or directing execution of one or more of the instructions, processes, and/or operations described herein. Processor 1604 may perform operations by executing computer-executable instructions 1612 (e.g., an application, software, code, and/or other executable data instance) stored in storage device 1606.

Storage device 1606 may include one or more data storage media, devices, or configurations and may employ any type, form, and combination of data storage media and/or device. For example, storage device 1606 may include, but is not limited to, any combination of the non-volatile media and/or volatile media described herein. Electronic data, including data described herein, may be temporarily and/or permanently stored in storage device 1606. For example, data representative of computer-executable instructions 1612 configured to direct processor 1604 to perform any of the operations described herein may be stored within storage device 1606. In some examples, data may be arranged in one or more databases residing within storage device 1606.

I/O module 1608 may include one or more I/O modules configured to receive user input and provide user output. I/O module 1608 may include any hardware, firmware, software, or combination thereof supportive of input and output capabilities. For example, I/O module 1608 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1608 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1608 is configured to provide graphical data to a display for presentation to a user. The graphical data may be representative of one or more graphical user interfaces and/or any other graphical content as may serve a particular implementation.

An illustrative system includes a brain interface system configured to be worn by a user and to output brain measurement data representative of brain activity of the user while the user is engaged in an electronic messaging session provided by an electronic messaging platform; and a computing device configured to obtain the brain measurement data, determine, based on the brain measurement data, a graphical emotion symbol representative of a mental state of the user while the user is engaged in the electronic messaging session, and provide the graphical emotion symbol for use during the electronic messaging session.

Another illustrative system includes a memory storing instructions; and a processor communicatively coupled to the memory and configured to execute the instructions to: obtain brain measurement data representative of brain activity of a user as output by a brain interface system while the user is engaged in an electronic messaging session provided by an electronic messaging platform; determine, based on the brain measurement data, a graphical emotion symbol representative of a mental state of the user while the user is engaged in the electronic messaging session; and provide the graphical emotion symbol for use during the electronic messaging session.

Another illustrative system includes a first brain interface system configured to be worn by a first user and to output first brain measurement data representative of brain activity of the first user while the first user is engaged in an electronic messaging session provided by an electronic messaging platform; a second brain interface system configured to be worn by a second user and to output second brain measurement data representative of brain activity of the second user while the second user is engaged in the electronic messaging session provided by the electronic messaging platform; and a computing device configured to obtain the first and second brain measurement data, determine, based on the first and second brain measurement data, one or more graphical emotion symbols representative of one or more mental states of the first and second users while the first and second users are engaged in the electronic messaging session, and provide the one or more graphical emotion symbols for use during the electronic messaging session.

An illustrative method includes obtaining, by a computing device, brain measurement data representative of brain activity of a user as output by a brain interface system while the user is engaged in an electronic messaging session provided by an electronic messaging platform; determining, by the computing device based on the brain measurement data, a graphical emotion symbol representative of a mental state of the user while the user is engaged in the electronic messaging session; and providing, by the computing device, the graphical emotion symbol for use during the electronic messaging session.

A non-transitory computer-readable medium storing instructions that, when executed, direct a processor of a computing device to: obtain brain measurement data representative of brain activity of a user as output by a brain interface system while the user is engaged in an electronic messaging session provided by an electronic messaging platform; determine, based on the brain measurement data, a graphical emotion symbol representative of a mental state of the user while the user is engaged in the electronic messaging session; and provide the graphical emotion symbol for use during the electronic messaging session.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a brain interface system configured to be worn by a user and to output brain measurement data representative of brain activity of the user while the user is engaged in an electronic messaging session provided by an electronic messaging platform; and a computing device configured to
obtain the brain measurement data,
determine, based on the brain measurement data, a graphical emotion symbol representative of a mental state of the user while the user is engaged in the electronic messaging session, and
provide the graphical emotion symbol for use during the electronic messaging session;

wherein the brain interface system comprises an optical measurement system configured to perform optical-based brain data acquisition operations, the brain measurement data based on the optical-based brain data acquisition operations, the optical measurement system comprising:

a wearable assembly configured to be worn by the user and comprising:
a first slot surrounded by a first wall;
a second slot surrounded by a second wall;
a first module comprising a first light source configured to emit first light directed at a brain of the user and a first set of detectors configured to detect first arrival times for photons of the first light after the first light is scattered by the brain, the brain measurement data based on the first arrival times; and
a second module comprising a second light source configured to emit second light directed at the brain and a second set of detectors configured to detect second arrival times for photons of the second light after the second light is scattered by the brain, the brain measurement data further based on the second arrival times;
wherein the first and second modules are configured to be interchangeably inserted into the first and second slots to acquire the brain measurement data.

2. The system of claim 1, wherein the first and second sets of detectors each comprise a plurality of single-photon avalanche diode (SPAD) circuits.

3. The system of claim 1, wherein the first and second modules are configured to be removably attached to the wearable assembly.

4. The system of claim 1, wherein the brain interface system is further configured to perform electrical-based brain data acquisition operations, the brain measurement data further based on the electrical-based brain data acquisition operations.

5. The system of claim 4, wherein the brain interface system further comprises:
a plurality of electrodes configured to be external to the user and detect electrical activity of the brain, the brain activity based on the arrival times and the electrical activity.

6. The system of claim 5, wherein the plurality of electrodes comprises a first electrode on a surface of the first module and a second electrode on a surface of the second module.

7. The system of claim 6, wherein the first electrode surrounds the first light source on the surface of the first module.

8. The system of claim 1, wherein the obtaining the brain measurement data, the determining the graphical emotion symbol, and the providing the graphical emotion symbol for use during the electronic messaging session are performed in substantially real time while the brain interface system outputs the brain measurement data.

9. The system of claim 1, wherein the obtaining the brain measurement data comprises receiving the brain measurement data from the brain interface system by way of one or more of a wired connection or a wireless connection.

10. The system of claim 1, wherein the computing device is included in the brain interface system.

11. The system of claim 1, wherein the determining the graphical emotion symbol comprises:
determining, based on the brain measurement data, the mental state of the user; and
selecting, from a library of graphical emotion symbols, a graphical emotion symbol that is associated with the mental state.

12. The system of claim 1, wherein the determining the graphical emotion symbol comprises:
determining, based on the brain measurement data, the mental state of the user; and
generating a custom graphical emotion symbol representative of the mental state.

13. The system of claim 1, wherein the determining the graphical emotion symbol is further based on one or more characteristics of the user.

14. The system of claim 1, wherein:
the brain interface system is further configured to output baseline brain measurement data while the user is not engaged in the electronic messaging session; and
the computing device is further configured to:
obtain the baseline brain measurement data; and
compare the brain measurement data with the baseline brain measurement data;
wherein the determining the graphical emotion symbol is based on the comparing of the brain measurement data with the baseline brain measurement data.

15. The system of claim 1, wherein:
the computing device is further configured to obtain sensor data representative of a sensed attribute of the user; and
the determining the graphical emotion symbol is further based on the sensor data.

16. The system of claim 1, wherein the providing the graphical emotion symbol for use during the electronic messaging session comprises including the graphical emotion symbol in an electronic message sent by the user to an additional user by way of the electronic messaging platform.

17. The system of claim 1, wherein the providing the graphical emotion symbol for use during the electronic messaging session comprises presenting the graphical emotion symbol to the user as an option for inclusion in an electronic message to be sent by the user.

18. The system of claim 1, wherein the providing the graphical emotion symbol for use during the electronic messaging session comprises presenting the graphical emotion symbol to one or more of the user or an additional user engaged in the electronic messaging session.

19. The system of claim 1, wherein the electronic messaging session comprises an extended reality experience.

* * * * *